United States Patent
Wang

(10) Patent No.: US 11,826,414 B2
(45) Date of Patent: Nov. 28, 2023

(54) MEASUREMENT OF AFUCOSYLATED IGG FC GLYCANS AND RELATED VACCINATION METHODS

(71) Applicants: CZ Biohub SF LLC, San Francisco, CA (US); The Board of Trustees of the Leland Stanford Junior University, Stanford, CA (US)

(72) Inventor: Taia T. Wang, Stanford, CA (US)

(73) Assignees: CZ Biohub SF, LLC, San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 591 days.

(21) Appl. No.: 16/758,364

(22) PCT Filed: Oct. 22, 2018

(86) PCT No.: PCT/US2018/056940
§ 371 (c)(1),
(2) Date: Apr. 22, 2020

(87) PCT Pub. No.: WO2019/083904
PCT Pub. Date: May 2, 2019

(65) Prior Publication Data
US 2020/0261564 A1    Aug. 20, 2020

Related U.S. Application Data

(60) Provisional application No. 62/583,369, filed on Nov. 8, 2017, provisional application No. 62/575,868, filed on Oct. 23, 2017.

(51) Int. Cl.
*A61K 39/12* (2006.01)
*A61P 31/14* (2006.01)
*C07K 16/10* (2006.01)
*G01N 33/569* (2006.01)
*G01N 33/68* (2006.01)

(52) U.S. Cl.
CPC ............ *A61K 39/12* (2013.01); *A61P 31/14* (2018.01); *C07K 16/1081* (2013.01); *G01N 33/56983* (2013.01); *G01N 33/6854* (2013.01); *G01N 2333/185* (2013.01); *G01N 2469/20* (2013.01)

(58) Field of Classification Search
None
See application file for complete search history.

(56) References Cited

FOREIGN PATENT DOCUMENTS

WO    2017/189891 A1    11/2017

OTHER PUBLICATIONS

Morrison et al., The Journal of Infectious Diseases, 2010, 201:370-377. (Year: 2010).*
Watanaveeradej et al., Am. J. Trop. Med. Hyg., 2011, 85(2):341-351. (Year: 2011).*
Boonnak et al., "Human FcγRII Cytoplasmic Domains Differentially Influence Antibody-Mediated Dengue Virus Infection", The Journal of Immunology, Jun. 1, 2013, pp. 5659-5665, vol. 190, No. 11, The American Association of Immunologists, Inc., Rockville, Maryland.
Dejnirattisai et al., "Dengue virus sero-cross-reactivity drives antibody-dependent enhancement of infection with zika virus", Nature Immunology, Jun. 23, 2016, pp. 1102-1108, vol. 17, No. 9, Springer Nature Limited, Berlin, Germany.
Ebbinghaus et al., Functional and Selective Targeting of Adenovirus to High-Affinity Fcγ Receptor I-Positive Cells by Using a Bispecific Hybrid Adapter, Journal Of Virology, Jan. 1, 2001, pp. 480-489, vo 1 . 75, No. 1, American Society for Microbiology, Washington, D.C.
Kanesa-Thasan et al., "Atypical antibody responses in dengue vaccine recipients", American Journal Of Tropical Medicine & Hygiene, American Society Of Tropical Medicine And Hygiene, Dec. 1, 2003, pp. 32-38, vol. 69, No. 6 Suppl, Ingenta, Oxford, United Kingdom.
Li et al., "Targeting the Fc receptor in autoimmune disease", Expert Opinion On Therapeutic Targets, Feb. 13, 2014, pp. 335-350, vol. 18, No. 3, Informa UK Limited, London, England, United Kingdom.
Li et al., Modulating IgG effector function by Fc glycan engineering, Proceedings Of The National Academy Of Sciences Of The United States Of America, Mar. 13, 2017, pp. 3485-3490, vol. 114, No. 13, National Academy of Sciences, Washington, D.C.
Littaua et al., "Human IgG Fc receptor II mediates antibody-dependent enhancement of dengue virus infection", The Journal Of Immunology, The American Association Of Immunologists, Apr. 15, 1990, pp. 3183-3186, vol. 1, 144, No. 8, The American Association of Immunologists, Inc., Rockville, Maryland.
Wang et al., "IgG antibodies to dengue enhanced for FcγRIIIA binding determine disease severity", Science, Jan. 27, 2017, pp. 395-398, vol. 355, No. 6323, American Association for the Advancement of Science, Washington, D.C.
Application PCT/US2018/056940, International Search Report and Written Opinion, dated Mar. 22, 2019, 14 Pages.

\* cited by examiner

*Primary Examiner* — Nicole Kinsey White
(74) *Attorney, Agent, or Firm* — Kilpatrick Townsend & Stockton LLP

(57) ABSTRACT

The present disclosure provides methods related to determining the level of afucosylated Fc glycans in IgG antibodies in a biological sample from a subject. This level can be used in methods aimed at monitoring and/or treating subject suffering from an acute flavivirus infection and/or who are at risk for progression to clinically significant infection or disease. This level can also be used in a vaccination method to ensure that those who receive a flavivirus vaccine have a reduced risk of reacting to the vaccine be developing clinically significant infection or disease. The disclosure also provides treatment methods based on inhibiting FcγRIIA or FcγRIIIA receptor signaling. Also provided are novel cell lines that are useful in measuring afucosylated Fc glycans.

9 Claims, 11 Drawing Sheets

Specification includes a Sequence Listing.

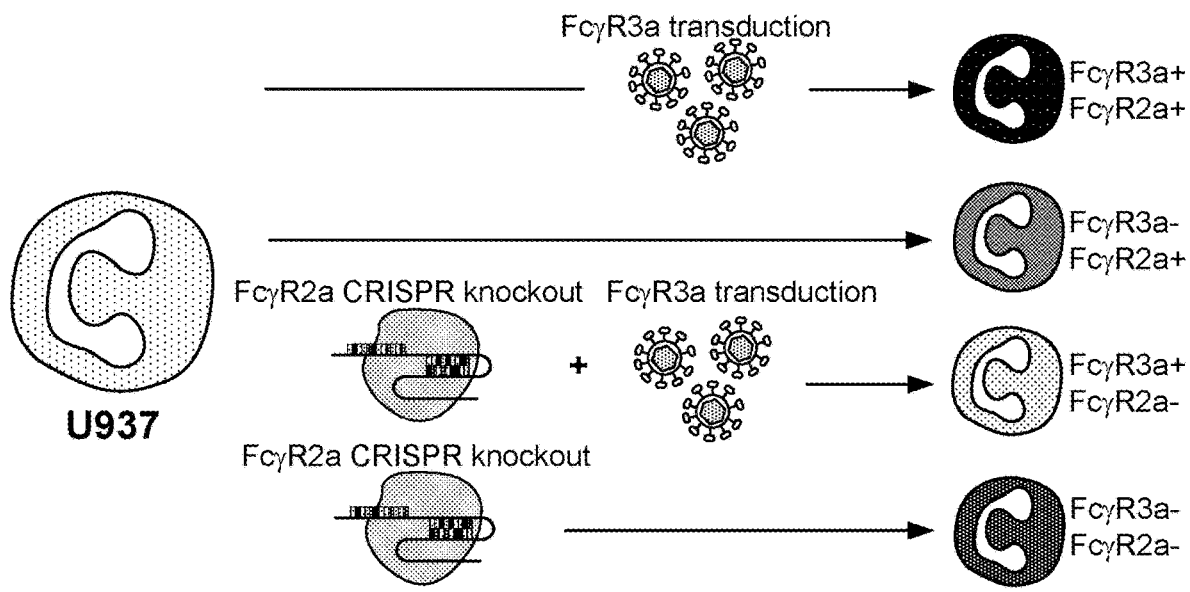
FIGURE 5
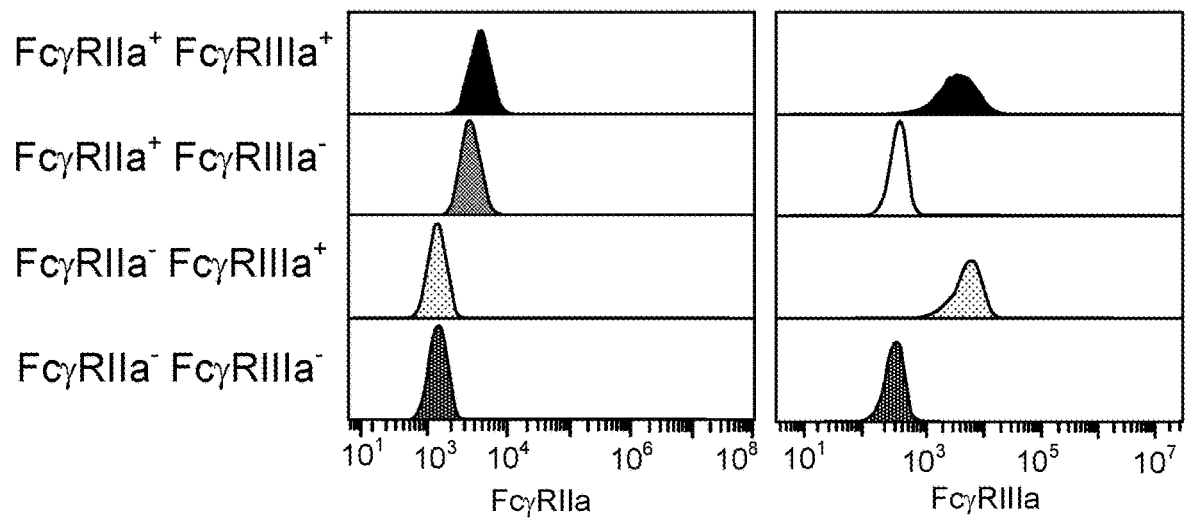
FIGURE 6A　　FIGURE 6B

SEQUENCE LISTING

```
<160> NUMBER OF SEQ ID NOS: 6

<210> SEQ ID NO 1
<211> LENGTH: 2429
<212> TYPE: DNA
<213> ORGANISM: Homo sapiens

<400> SEQUENCE: 1
ctcttttcta agcttgtctc ttaaaaccca ctggacgttg gcacagtgct gggatgacta      60
tggagaccca aatgtctcag aatgtatgtc ccagaaacct gtggctgctt caaccattga     120
cagttttgct gctgctggct tctgcagaca gtcaagctgc agctccccca aaggctgtgc     180
tgaaacttga gcccccgtgg atcaacgtgc tccaggagga ctctgtgact ctgacatgcc     240 aggggctcg cagccctgag agcgactcca ttcagtggtt ccacaatggg aatctcattc      300
ccacccacac gcagcccagc tacaggttca aggccaacaa caatgacagc ggggagtaca     360
cgtgccagac tggccagacc agcctcagcg accctgtgca tctgactgtg ctttccgaat     420
ggctggtgct ccagaccct cacctggagt tccaggaggg agaaaccatc atgctgaggt      480
gccacagctg gaaggacaag cctctggtca aggtcacatt cttccagaat ggaaaatccc     540
agaaattctc ccatttggat cccaccttct ccatcccaca agcaaaccac agtcacagtg     600
gtgattacca ctgcacagga aacataggct acacgctgtt ctcatccaag cctgtgacca     660
tcactgtcca agtgccagc atgggcagct cttccaccat ggggatcatt gtggctgtgg      720
tcattgcgac tgctgtagca gccattgttg ctgctgtagt ggccttgatc tactgcagga     780
aaaagcggat ttcagccaat tccactgatc ctgtgaaggc tgcccaattt gagccacctg     840
gacgtcaaat gattgccatc agaaagagac aacttgaaga aaccaacaat gactatgaaa     900
cagctgacgg cggctacatg actctgaacc ccaggcacc tactgacgat gataaaaaca     960
tctacctgac tcttcctccc aacgaccatg tcaacagtaa taactaaaga gtaacgttat    1020
gccatgtggt catactctca gcttgctgag tggatgacaa aaagagggga attgttaaag    1080
gaaaatttaa atggagactg gaaaaatcct gagcaaacaa aaccacctgg cccttagaaa    1140
tagctttaac tttgcttaaa ctacaaacac aagcaaaact tcacggggtc atactacata    1200
caagcataag caaaacttaa cttggatcat ttctggtaaa tgcttatgtt agaaataaga    1260
caaccccagc caatcacaag cagcctacta acatataatt aggtgactag ggactttcta    1320
agaagatacc taccccaaa aaacaattat gtaattgaaa accaaccgat tgcctttatt     1380
ttgcttccac attttcccaa taaatacttg cctgtgacat tttgccactg gaacactaaa    1440
```

-continued

```
cttcatgaat tgcgcctcag attttcctt taacatcttt ttttttttg acagagtctc      1500 aatctgttac ccaggctgga gtgcagtggt gctatcttgg ctcactgcaa acccgcctcc      1560
caggtttaag cgattctcat gcctcagcct cccagtagct gggattagag gcatgtgcca      1620
tcatacccag ctaattttg tatttttat tttttttt tagtagagac agggtttcgc      1680
aatgttggcc aggccgatct cgaacttctg gcctctagcg atctgcccgc ctcggcctcc      1740
caaagtgctg ggatgaccag catcagcccc aatgtccagc ctctttaaca tcttctttcc      1800
tatgccctct ctgtggatcc ctactgctgg tttctgcctt ctccatgctg agaacaaaat      1860
cacctattca ctgcttatgc agtcggaagc tccagaagaa caaagagccc aattaccaga      1920
accacattaa gtctccattg ttttgccttg ggatttgaga agagaattag agaggtgagg      1980
atctggtatt tcctggacta aattcccctt ggggaagacg aagggatgct gcagttccaa      2040
aagagaagga ctcttccaga gtcatctacc tgagtcccaa agctccctgt cctgaaagcc      2100
acagacaata tggtcccaaa tgactgactg caccttctgt gcctcagccg ttcttgacat      2160
caagaatctt ctgttccaca tccacacagc aatacaatt agtcaaacca ctgttattaa      2220
cagatgtagc aacatgagaa acgcttatgt tacaggttac atgagagcaa tcatgtaagt      2280
ctatatgact tcagaaatgt taaaatagac taacctctaa caacaaatta aaagtgattg      2340
tttcaaggtg atgcaattat tgatgaccta ttttattttt ctataatgat catatattac      2400
ctttgtaata aaacattata accaaaaca                                          2429

<210> SEQ ID NO 2
<211> LENGTH: 8865
<212> TYPE: DNA
<213> ORGANISM: Homo sapiens

<400> SEQUENCE: 2
ggagccccgg ctcctaggct gacagaccag cccagatcca gtggcccgga ggggcctgag        60
ctaaatccgc aggacctggg taacacgagg aaggtaaaga gttcctgtcc tcgcccctcc      120 ccaccccac cttttctgtg atcttttcag cctttcgctg gtgacttgtt cttccagggc      180
ccatttctct acccctacctg ggtttcttct aacctggaaa tctaatgatc aaatcacact      240
aaaaagtcag tagctcctgt ggattacata tcccaggagc atatagattt tgaattttga      300 atttgaaag aaattctgcg tggagataat attgaggcag agacactgct agtggtctga      360
agatttgaaa ggaccacttt ctgtgtgcag gcagggcctc agctggagat agatgggtct      420
gggcgaggca ggagagtgac aagttctgag gtgaaatgaa ggaagccctc agagaatgct      480
cctcccacct tgaatctcat ccccagggtc tcactgtccc attcttggtg ctgggtggat      540
ccaaatccag gagatggggc aagcatcctg ggatggctga gggcacactc tggcagattc      600
tgtgtgtgtc ctcagatgct cagccacaga cctttgaggg agtaaagggg gcagacccac      660
ccaccttgcc tccaggctct ttccttcctg gtcctgttct atggtggggc tcccttgcca      720
gacttcagac tgagaagtca gatgaagttt caagaaaagg aaattggtgg gtgacagaga      780
tgggtggagg ggctggggaa aggctgttta cttcctcctg tctagtcggt ttggtccctt      840
tagggctccg gatatctttg gtgacttgtc cactccagtg tggcatcatg tggcagctgc      900
tcctcccaac tgctctgcta cttctaggta agtcagggtc tccctggttg agggagaagt      960
ttgagatgcc ttgggttcag cagagacccc ttttcaggct acgaatgaga ctcccacgaa     1020
gggatgggac ccctcaccac atctatagct gtggattgag ctcctaggac aagccaagat     1080
ggggctagaa atgaggagaa tgctggttcc aattggggca tactcatgag tgaggccagt     1140
```

```
cacttcaccc ctctgggtcc cagaatcact ctgtggaacc aaagagcttc gactagatgg   1200
tccctagggt ctgtctcttt cagtttgaca ttccagggtt ctcctctatg attttcaatt   1260
tctacccttt cttgtgggga tatgggttga ggctctttct gtagcttggt tcagggaaat   1320
tcaacctgta cccttaattt gtgagtttgc acagggagca aggggtaagg gagcagtgtt   1380
gaaaataggg atttgtgttg acagtggcgc aagaggcatg aacagtggag accagagagc   1440
aggtagcaag gtttccacca gaaacatcct gattcttggg aaaattgggc tcctggggca   1500
gaggagggca ggggagtttt aaactcactc tatgttctaa tcactctgat ctctgcccct   1560
actcaatatt tgatttatct tttttcttgc agtttcagct ggcatgcgga ctggtgagtc   1620
agcttcatgg tcttggattg acccagtggg gcacatatgg ggacaaaggc cataagatat   1680
tgggaaatgc ttgttgaatg ggaaaatgct gatgtggggt tagcagggat agttcctcca   1740
acacagcaga acttggccct gtgcttctct ggccagcttt ccttaagata ctgaacaggc   1800
caaaaatggg gccaagatgc tctaagactg agccaccaag catgggtttg caatgagctc   1860
attctggctt tgaggctccc tgggaatggc agtgtagagc ctgctcctct ccctgtcctc   1920
accccacatt atcttggctc ctcagaagat ctcccaaagg ctgtggtgtt cctggagcct   1980
caatggtaca gggtgctcga aaggacagt gtgactctga agtgccaggg agcctactcc   2040
cctgaggaca attccacaca gtggtttcac aatgagagcc tcatctcaag ccaggcctcg   2100
agctacttca ttgacgctgc cacagtcgac gacagtggag agtacaggtg ccagacaaac   2160
ctctccaccc tcagtgaccc ggtgcagcta aagtccata tcggtgagtt gatgaagggg   2220
aagaggaaaa tcaccaataa agggtgaaac aaagggtcct gaaatacttg gtaagagcca   2280
gagatgatat tcttagagat aaaagctaag atgagatgat gtgtggtccc actgaatggt   2340
atcagagttg tagtcctagc tctaagtagg tcttgggcaa aatgtcaaag cctgtcagac   2400
agtagatata ggactgctgc attgcacaat tccaagaatc cccatatgga gtgcatacaa   2460
tgtgaatgtg tcatgtgaag gttaggccat ggcatagatg ctcaataata gttatttata   2520
tatttatttt cattttttt aattttattt tttgagacag agtatcactc tgtcacccag   2580
gctggagtgc aatgcggcaa tctcagctca ctgcaacttc tgcccccttg ggttgtagtg   2640
attctcctgc ctcagcctcc cgagtagctg agattacagg caccgccac cacgcccagc   2700 taattttttgt attttagta gagacagggt ttcaccatgt tggtcagtct ggtctcaaac   2760
tcctgacctc aggtgattca ccagccttgg cttcccaaag tgctggggact acaggcgtga   2820 gccaccacac ctggccaata atatttattg aataaattaa tgaatttggt gttaggacct   2880
caatctcctt ctcgctctca gacatgtaat gccctaagcc acctcccaaa gcaatcctag   2940
tggcctagca tcatatcttt ctgtctcctc atcaatgcta tactcaaacc tataattaag   3000
cataaatttg gtaatgtgat agctcttcca atagaggcag atacatgttc agcctgcaca   3060
ttaatcatga catgaaagtt cttgtgtact attaacagaa tatagacgtc agacacaggt   3120
aggagaaata ttttgaaggc agaggtctttt cctggtgtcc ctacaatctt accacatagg   3180
ctggtccctg cagtgtcgcc ctgcaaacct aactctactt ccacggctgt tccattcata   3240
caatgtttat gggtggaaca agctttgggg gaagaagggc ataaggaggt ggatctgcaa   3300
gagagctcca tggaattggg cctctgaaac tgattttgt ggctcttgg cctctgacag   3360 taccactcaa ctgacatggt cttcactctc cagagctaca agaagatatg tccatttcta   3420
gctaggtaag agatgtccac ctacaaccaa ataaaatggg ggaattacca agagaaagca   3480
```

```
atagaaaaat caagtctaag agttactagt ttgccttgaa cttggctcta gaaactggct      3540
ttagaagtct agccaatcaa ggctatatta aactgtgacc atgagaatta gcttcaccag      3600
gtaaacttct gagcatcctt taatccttta ggacccattt cacttatgtc ctcctctgag      3660
aagcattttt tacttctttt tttgtttgtt tgtttgtgtt tgttttgtt tttgtttttg       3720 agacagagtc tctctctgtc acccaagctg gagtgcagtg gcgcaatctt ggctcactgc      3780
aacctccacc tcccgggttc aagcaattct cctgcctcag cctcccaagt agctgggact      3840
acaggtgcat gccaccacgc ccggctaatt ttttgtattt ttagtagaga cagggtttcg      3900
cagcgttagc caggatggtc ttgatctcct gacttcatga tctgcccacc tcggcctccc      3960
aaagtactag gattacagat gtgagccacc gcgcccagcc tgcatttttt acttctttca      4020
ggcagaattt ctttattcca atctagtcag ccccgcagtc ctttattctt agcctgttgt      4080
agcacttgtc atattgtatt gtgattattt ctgaatattt atgtttctat gtctagactg      4140
tagattcttt gaggctgaga actatatgtc ccatcatctg ggtatctcca gtccacagtg      4200
tgtcatacat agtgagtgct tgatgaaata tcacttgaag gaatatacat atggacattc      4260
actgggtcca tgacaggata gattcgaaca agaatgttcc tccaaaggcc accagactat      4320
atactaacca tgactttatg ctaataatga ttcatctctc tgctgaaaaa gtaagtggat      4380
agataggcac atggcttctt ttgataaatg atatctctta ataggtaatg aagattactt      4440
tctgtttggc aaatctttgt ggtagagaat catgaccaac acacgtccta ccaatttgt       4500 ttagcatcag gtagtagatt ttttaaatta tagtaattca agctgagaat gtagatttaa      4560
aaaataaaat tattgtaaat tttgttttgt tcttattaca aaagtcattt ggggtcaatt      4620
tcaaaaatat ataaaagtaa acaggagaaa tttaaaatgt ccttcagtcc cactccttca      4680
gagaaaaccc ctgttaatat gtaagtgcat atccttcttt tttctgtgca taatactttt      4740
taaaatattt gaagtattat gcttttttaa cttaaaattg tctcatgaat attttcttat      4800
gccattataa tacttaccta taacatcatt attttttaat tattcaggcc ctttcccgac      4860
catgacctca tgttctctct ttgtgaagtc tgattacttg gtgacatgat cgtgagaata      4920
agctctggcg atataagaat ttcctctctt gaaggccatg ctcagtaaat tacttggtga      4980
catgatcgtg agaataagct ctggcgatac aagaatttcc tctcttgaag gccatgctca      5040
gtaataaagt tggtctcacc gaggccctgt gacaccttag aaaccacgaa ttgccaggct      5100
gagcaatacc agtcccgccc ttcccctccc tggtgtttac attgagttct ccttcacaat      5160
ttctgcagcc actccgtggc caccgtcacc ttattcctga ctgccacaag agtctttcaa      5220
tattcctttg attgcctatt ccttctgaaa tctacctttt cctctaatag ggcaattcat      5280
cattttcaaa tgcaattttt actctgatct agaacttact gtgaatcctt gtcacctgcc      5340
acagcaaatc taagtctagc acttaaggat cctgcagata tgctcatcgt tgcttctcac      5400
ttacctcatt gcttagtccc tctgctctaa ccctgtgtgt tgatcacatg tgtgtgtgtc      5460
cctcttcccc attagacaaa ggtcttggta tgacttcagt tctcttgcag ggccccatca      5520
gctcttcccc aaagggagct atgcagggtt gactcccaat ctggctttcc cttatgtctc      5580
aggatctggg tggtacgtgg ccccttcaca aagctctgca ctgagagctg aggcctcccg      5640
ggcctggggt gtctgtgtct ttcaggctgg ctgttgctcc aggcccctcg gtgggtgttc      5700
aaggaggaag accctattca cctgaggtgt cacagctgga agaacactgc tctgcataag      5760
gtcacatatt tacagaatgg caaaggcagg aagtattttc atcataattc tgacttctac      5820
attccaaaag ccacactcaa agacagcggc tcctacttct gcaggggggct ttttgggagt      5880
```

```
aaaaatgtgt cttcagagac tgtgaacatc accatcactc aaggtgagac atgtgccacc   5940
ctggaatgcc cagggacgcc tgtgtgtgga acctgcaatc acactgggaa gttgagttgg   6000
gaggagattc ctgattctta cacgcacttc ttcatatgtg gttccctcct ggtgatcacc   6060
aggaggtccc caaaagtccc tgattgcagg gtaggtttgc agctctgttt cagtccattc   6120
ttttggggta gctaggaggt gtcattcact ctgcagcatg atggcaggag cagaagccac   6180
atctcctccc caataaatac ctctgtcttt ccttacgcta atcacaccca cggtgtcata   6240
tgttcctatc gtgctggcct ccttcttatc caagcctttt agccacgatc caaactggca   6300
ggagcccctc atccctcac agaaagagcc cagaacctgg gttctggccc tgcagctaat    6360
taaccatctg accagaggtg agccacttag tctctctgaa ccccaatttc ttcttccgta   6420
acaaaaataa gctgacattt attgggcacc tttcagtgtg ctagactctg tgctaaacaa   6480
ttctttacat gcacctggtt tgactatcac agtagacctt cacaacatga gataggtaat   6540
attccatttt acagatgaag taaccgaggt gcaaaaataa ataataagt ttccctaagg     6600 tcacatcaaa gacttcaaag cctgtatatt taaccagtaa gtaaaagatt tgaacaagca   6660
ctaatatcct atgatcccat taagtcatcc acaaaacatc tctaggttct gtagcaccag   6720
cctccagaat cagagctcta gagtggtgtg cctggacttt ccagtttcac agaacttcta   6780
tctgtaacta gcccaagaca taaattgtaa acaatttgca tgtagaaagg cagcaaaaca   6840
ccttttgaga ttttgacact acaatgccat aatttgtaca aaaataattt catgacactt    6900
taaactgaaa gtaaatactc ccaagtggtt agggaaagag agcaaataaa gcaaatgggg   6960
taacatgtaa acaatgagtg gatctgggta aaggatatac gagattaaac tattctggtc   7020 atttttttt taagtttgga aatatatcaa aatcaagagt ttaaaaaatt gaaatgcaaa    7080
atcaacaaat ttgtcccagt ttctagacca tagcattgtc tgacaatttc ttaactgtca   7140
cacaaaaccc agcttacaac ctaacttgtt aacgctccct gtcacatctc tgtcaaacaa   7200
gcaggagcct ttgctcagtg tttggtgagc tgtcctctgc tcagatagca ctaagatcag   7260
gaaccaatgg gaggaagcaa tactttcccc cagacttccc caccattcct accacttgcc   7320
tgttggctgt tgtcaaagac tttctactgg tgacctcact gtttgttcca aatatctgcc   7380
ttagtgactg tcatttttt tcatctctcc acttctccta ataggtttgg cagtgtcaac     7440
catctcatca ttcttttccac ctgggtacca agtctctttc tgcttggtga tggtactcct   7500
ttttgcagtg gacacaggac tatatttctc tgtgaagaca aacattcgaa gctcaacaag   7560
agactggaag gaccataaat ttaaatggag aaaggaccct caagacaaat gacccccatc   7620 ccatggggt aataagagca gtagcagcag catctctgaa catttctctg gatttgcaac     7680
cccatcatcc tcaggcctct ctacaagcag caggaaacat agaactcaga gccagatccc   7740
ttatccaact ctcgactttt ccttggtctc cagtggaagg gaaaagccca tgatcttcaa   7800
gcagggaagc cccagtgagt agctgcattc ctagaaattg aagtttcaga gctacacaaa   7860
cactttttct gtcccaaccg ttccctcaca gcaaagcaac aatacaggct agggatggta   7920
atcctttaaa catacaaaaa ttgctcgtgt tataaattac ccagtttaga ggggaaaaaa   7980
aaacaattat tcctaaataa atggataagt agaattaatg gttgaggcag gaccatacag   8040
agtgtgggaa ctgctgggga tctagggaat tcagtgggac caatgaaagc atggctgaga   8100
aatagcaggt agtccaggat agtctaaggg aggtgttccc atctgagccc agagataagg   8160
gtgtcttcct agaacattag ccgtagtgga attaacagga aatcatgagg gtgacgtaga   8220
```

-continued

```
attgagtctt ccaggggact ctatcagaac tggaccatct ccaagtatat aacgatgagt    8280
cctcttaatg ctaggagtag aaaatggtcc taggaagggg actgaggatt gcggtggggg    8340
gtggggtgga aagaaagta cagaacaaac cctgtgtcac tgtcccaagt tgctaagtga     8400
acagaactat ctcagcatca gaatgagaaa gcctgagaag aaagaaccaa ccacaagcac    8460
acaggaagga aagcgcagga ggtgaaaatg ctttcttggc cagggtagta agaattagag    8520
gttaatgcag ggactgtaaa accaccttt ctgcttcaat atctaattcc tgtgtagctt     8580
tgttcattgc atttattaaa caaatgttgt ataaccaata ctaaatgtac tactgagctt    8640
cgctgagtta agttatgaaa ctttcaaatc cttcatcatg tcagttccaa tgaggtgggg    8700
atggagaaga caattgttgc ttatgaaaga aagctttagc tgtctctgtt ttgtaagctt    8760
taagcgcaac atttcttggt tccaataaag cattttacaa gatcttgcat gctactctta    8820
gatagaagat gggaaaacca tggtaataaa atatgaatga taaaa                    8865
```

```
<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gatgtatgtc ccagaaacct g                                              21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
gcatatgacc ccaaggctgg g                                              21

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Val Ile Val Ile Thr
1               5

<210> SEQ ID NO 6
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 6

Val Glu Glu Thr
1
```

MEASUREMENT OF AFUCOSYLATED IGG FC GLYCANS AND RELATED VACCINATION METHODS

CROSS-REFERENCE TO RELATED APPLICATIONS

This application is a National Stage application of International Application PCT/US2018/056940, filed Oct. 22, 2018, which published as WO/2019/083904 on May 2, 2019, and which claims the priority benefit of U.S. provisional application no. 62/575,868, filed Oct. 23, 2017, and U.S. provisional application no. 62/583,369, filed Nov. 8, 2017, which are hereby incorporated by reference in their entireties for all purposes.

SEQUENCE LISTING

This application contains a Sequence Listing which has been submitted electronically in ASCII format and is hereby incorporated by reference in its entirety. The ASCII copy, created on Apr. 29, 2019, is named CZBHP001WO_SL.txt and is 159,304 bytes 16 KB in size.

STATEMENT AS TO RIGHTS TO INVENTIONS MADE UNDER FEDERALLY SPONSORED RESEARCH AND DEVELOPMENT

Not applicable.

FIELD

The present disclosure relates generally to the area of the role of afucosylated Fc glycans in disease. In particular, the disclosure relates to methods for vaccinating against and treating flaviviral infection.

BACKGROUND

IgG antibodies represent a key link between the adaptive and innate immune systems. The ability of an IgG antibody to mediate a biological effect in vivo results from their bispecific nature. While the IgG Fab domain binds to the antigen, the Fc domain can modulate cellular effector functions through interactions with Fc receptors (FcγRs) on immune cells (FIG. 1A, FIG. 2). Fc-FcγR interactions can result in positive regulatory mechanisms such as the activation of antibody-dependent cellular cytotoxicity, phagocytosis, and pro-inflammatory cytokine production, as well as negative regulatory functions, such as inhibition of inflammatory immune responses. In rare settings, such as dengue virus (DENV) infections that occur in the presence of reactive, non-neutralizing IgGs, FcγRs can also mediate uptake of virus particles and cellular changes resulting in antibody-dependent enhancement (ADE) of DENV infection [1, 2].

While traditionally considered to be the invariant region of an IgG molecule, the Fc domain displays considerable heterogeneity, arising both from amino acid differences among the different IgG subclasses and the heterogeneity of the N-linked, complex, biantennary glycan associated with the CH2 domain of the IgG (FIG. 1B). There are four subclasses of IgGs (IgG1-4), with IgG1 and IgG3 having the highest activating FcγR binding affinities [3]. The most biologically significant modifications to Fc glycan composition are sialylation and fucosylation: glycans lacking sialic acid and core fucose (afucosylated) confer highest affinity for the activating Type I FcγRIIIA, which is expressed on NK cells, monocytes and macrophages. Glycans that are modified by sialic acids, confer binding affinity for Type II FcγRs that have various modulatory activities [4].

SUMMARY

Various embodiments contemplated herein may include, but need not be limited to, one or more of the following:

Embodiment 1

A method of analyzing antibodies, wherein the method includes determining the level of afucosylated Fc glycans in IgG antibodies in a biological sample from a subject acutely infected with a flavivirus or from a maternal subject having an infant acutely infected with a flavivirus, wherein the subject has not been determined to have an autoimmune disorder.

Embodiment 1a

A method of determining the susceptibility of a subject to clinically significant flaviviral infection or disease, the method comprising determining the level of afucosylated Fc glycans in IgG antibodies in a biological sample from the subject, wherein an elevated level of afucosylated Fc glycans in the biological sample indicates that the subject is susceptible to clinically significant flaviviral infection or disease.

Embodiment 2

The method of embodiment 1 or 1a, wherein the IgG antibodies are IgG1 antibodies.

Embodiment 3

The method of embodiment 1 or 1a or embodiment 2, wherein the IgG antibodies are IgG antibodies of all specificities.

Embodiment 4

The method of embodiment 1 or 1a or embodiment 2, wherein the IgG antibodies are IgG antibodies specific for a flaviviral antigen.

Embodiment 5

The method of embodiment 4, wherein the flaviviral antigen is a dengue viral antigen.

Embodiment 6

The method of embodiment 4, wherein the flaviviral antigen is a Zika viral antigen.

Embodiment 7

The method of any one of embodiments 1-6, wherein the subject is a human.

Embodiment 8

The method of embodiment 7, wherein the subject has the acute flaviviral infection in the presence of preexisting IgG antibodies that are reactive with the infecting flavivirus.

Embodiment 9

The method of embodiment 7, wherein the subject is a maternal subject having an infant.

Embodiment 9a

The method of embodiment 9, wherein the infant is acutely infected with a flavivirus.

Embodiment 10

The method of embodiment 9 or 9a, wherein the maternal subject has IgG antibodies that are reactive with the infecting flavivirus.

Embodiment 11

The method of any one of embodiments 1-10, wherein the biological sample is blood or a blood fraction.

Embodiment 12

The method of any one of embodiments 1-11, the method including monitoring the subject or infant for progression to clinically significant flaviviral infection or disease based on an elevated level of afucosylated Fc glycans in the biological sample.

Embodiment 13

The method of any one of embodiments 1-12, wherein the subject or infant is one that has tested positive for a flaviviral infection.

Embodiment 14

The method of embodiment 12 or embodiment 13, wherein the method includes hospitalizing the subject or infant based on having an elevated level of afucosylated Fc glycans in the biological sample.

Embodiment 15

The method of any one of embodiments 12-14, wherein the flavivirus is a dengue virus, and the clinically significant flaviviral infection or disease includes severe dengue disease.

Embodiment 16

The method of embodiment 15, wherein the method includes treating the subject or infant to prevent or inhibit progression to, or to manage, severe dengue disease, based on an elevated level of afucosylated Fc glycans in the biological sample.

Embodiment 17

The method of embodiment 16, wherein the treatment includes transfusion with blood and/or platelets.

Embodiment 18

The method of any one of embodiments 12-17, wherein the method includes administering one or more doses of neutralizing anti-flavivirus IgG, wherein the percentage of fucosylated Fc regions in each dose is greater than 95%.

Embodiment 19

A method of treating a subject or infant having at least one symptom of infection with a flavivirus, wherein the subject or the mother of the infant has been determined to have an elevated level of afucosylated Fc glycans by assaying a biological sample from the subject or mother, the method including monitoring the subject or infant for progression to clinically significant flaviviral infection or disease.

Embodiment 20

The method of embodiment 19, wherein the subject or infant is one that has tested positive for a flaviviral infection.

Embodiment 21

The method of embodiment 19 or embodiment 20, wherein the IgG antibodies are IgG1 antibodies.

Embodiment 22

The method of any one of embodiments 19-21, wherein the IgG antibodies are IgG antibodies of all specificities.

Embodiment 23

The method of any one of embodiments 19-21, wherein the IgG antibodies are IgG antibodies specific for a flaviviral antigen.

Embodiment 24

The method of embodiment 23, wherein the flaviviral antigen is a dengue viral antigen.

Embodiment 25

The method of embodiment 23, wherein the flaviviral antigen is a Zika viral antigen.

Embodiment 26

The method of any one of embodiments 19-25, wherein the elevated level of afucosylated Fc glycans is defined as 5 percent or greater.

Embodiment 27

The method of embodiment 26, wherein the elevated level of afucosylated Fc glycans is defined as 10 percent or greater.

Embodiment 28

The method of any one of embodiments 19-27, wherein the subject is a human.

Embodiment 29

The method of embodiment 28, wherein the subject has the acute flaviviral infection in the presence of preexisting IgG antibodies that are reactive with the infecting flavivirus.

Embodiment 30

The method of embodiment 28, wherein the subject is a maternal subject having an infant acutely infected with a flavivirus.

Embodiment 31

The method of embodiment 30, wherein the maternal subject has IgG antibodies that are reactive with the flavivirus infecting the infant.

Embodiment 32

The method of any one of embodiments 19-31, wherein the biological sample is blood or a blood fraction.

Embodiment 33

The method of any one of embodiments 19-32, wherein the method includes hospitalizing the subject or infant.

Embodiment 34

The method of any one of embodiments 19-33, wherein the flavivirus is a dengue virus, and the clinically significant flaviviral infection or disease includes severe dengue disease.

Embodiment 35

The method of embodiment 34, wherein the method includes treating the subject or infant to prevent or inhibit progression to, or to manage, severe dengue disease.

Embodiment 36

The method of embodiment 35, wherein the treatment includes transfusion with blood and/or platelets.

Embodiment 37

The method of any one of embodiment 19-36, wherein the method includes administering one or more doses of neutralizing anti-flavivirus IgG, wherein the percentage of fucosylated Fc regions in each dose is greater than 95%.

Embodiment 38

A vaccination method, the method including vaccinating a subject against a flavivirus if the subject has been determined not to have an elevated level of afucosylated Fc glycans in IgG antibodies in a biological sample from the subject or, in an infant subject, if the mother of the infant, has been determined not to have an elevated level of afucosylated Fc glycans in IgG antibodies in a biological sample from the mother.

Embodiment 39

The vaccination method of embodiment 38, wherein the IgG antibodies are IgG1 antibodies.

Embodiment 40

The method of embodiment 38 or embodiment 39, wherein the IgG antibodies are IgG antibodies of all specificities.

Embodiment 41

The vaccination method of any one of embodiment 38 or embodiment 39, wherein the IgG antibodies are IgG antibodies specific for a flaviviral antigen.

Embodiment 42

The vaccination method of embodiment 41, wherein the flaviviral antigen is a dengue viral antigen.

Embodiment 43

The vaccination method of embodiment 41, wherein the flaviviral antigen is a Zika viral antigen.

Embodiment 44

The vaccination method of any one of embodiments 38-43, wherein the elevated level of afucosylated Fc glycans is defined as 5 percent or greater.

Embodiment 45

The vaccination method of embodiment 44, wherein the elevated level of afucosylated Fc glycans is defined as 10 percent or greater.

Embodiment 46

The vaccination method of any one of embodiments 38-45, wherein the subject is a human.

Embodiment 47

The vaccination method of embodiment 46, wherein the subject is an infant.

Embodiment 48

The method of embodiment 47, wherein the mother of the infant has IgG antibodies that are reactive with the flavivirus.

Embodiment 49

The vaccination method of any one of embodiments 38-48, wherein the biological sample is blood or a blood fraction.

Embodiment 50

A method of treating a subject acutely infected with a flavivirus and at risk of progression to clinically significant flaviviral infection or disease, the method including administering to the subject an inhibitor of FcγRIIA or FcγRIIIA receptor signaling.

Embodiment 51

A method of reducing an immune response in a subject in need thereof, the method including administering to the subject an inhibitor of FcγRIIIA receptor signaling.

Embodiment 52

The method of embodiment 51, wherein the subject has an autoimmune disorder.

Embodiment 53

The method of any one of embodiments 50-52, wherein the inhibitor includes an inhibitor of binding between the Fc region of IgG antibodies and the FcγRIIA or FcγRIIIA receptor.

Embodiment 54

The method of any one of embodiments 50-52, wherein the inhibitor includes a nucleic acid inhibitor of expression of the FcγRIIA or FcγRIIIA receptor.

Embodiment 55

The method of any one of embodiments 50-54, wherein the inhibitor inhibits FcγRIIA and FcγRIIIA receptor signaling, or the method includes co-administering inhibitors of FcγRIIA and FcγRIIIA receptor signaling.

Embodiment 56

The method of any one of embodiments 50-55, wherein the subject has tested positive for a flaviviral infection.

Embodiment 57

The method of any one of embodiments 50-56, wherein the subject has been determined to have an elevated level of afucosylated Fc glycans by assaying a biological sample from the subject.

Embodiment 58

The method of embodiment 50, wherein the inhibitor includes therapeutic IgGs or Fc regions thereof that have a higher level of fucosylated Fc regions than the biological sample from the subject.

Embodiment 59

The method of embodiment 58, wherein the inhibitor includes a dose of neutralizing anti-flavivirus IgG, wherein the percentage of fucosylated Fc regions in the dose is greater than 95%.

Embodiment 60

The method of embodiment 57, wherein the IgG antibodies are IgG1 antibodies.

Embodiment 61

The method of embodiment 57 or embodiment 60, wherein the IgG antibodies are IgG antibodies of all specificities.

Embodiment 62

The method of embodiment 57 or embodiment 60, wherein the IgG antibodies are IgG antibodies specific for a flaviviral antigen.

Embodiment 63

The method of embodiment 62, wherein the flaviviral antigen is a dengue viral antigen.

Embodiment 64

The method of embodiment 62, wherein the flaviviral antigen is a Zika viral antigen.

Embodiment 65

The method of any one of embodiments 57-63, wherein the elevated level of afucosylated Fc glycans is defined as 5 percent or greater.

Embodiment 66

The method of embodiment 65, wherein the elevated level of afucosylated Fc glycans is defined as 10 percent or greater.

Embodiment 67

The method of any one of embodiments 50-66, wherein the subject is a human.

Embodiment 68

The method of embodiment 67, wherein the inhibitor of FcγRIIA or FcγRIIIA receptor signaling includes a humanized antibody.

Embodiment 69

The method of embodiment 68, wherein the subject has the acute flaviviral infection in the presence of preexisting IgG antibodies that are reactive with the infecting flavivirus.

Embodiment 70

The method of embodiment 68, wherein the subject is an infant.

Embodiment 71

The method of embodiment 70, wherein the infant has a mother who has IgG antibodies that are reactive with the infecting flavivirus.

Embodiment 72

The method of any one of embodiments 50-71, wherein the biological sample is blood or a blood fraction.

Embodiment 73

The method of any one of embodiments 50-72, wherein said treating additionally includes hospitalizing the subject.

Embodiment 74

The method of any one of embodiments 50-73, wherein the flavivirus is a dengue virus, and the clinically significant flaviviral infection or disease includes severe dengue disease.

Embodiment 75

The method of embodiment 74, wherein said treating includes treatment to prevent or inhibit progression to, or to manage, severe dengue disease.

Embodiment 76

The method of embodiment 75, wherein said treating includes transfusion with blood and/or platelets.

Embodiment 77

A cell line that does not express a FcγRIIA receptor or does not express a FcγRIIIA receptor.

Embodiment 78

The cell line of embodiment 77, wherein the cell line does not express the FcγRIIA receptor.

Embodiment 79

The cell line of embodiment 78, wherein the cell line expresses the FcγRIIIA receptor.

Embodiment 80

The cell line of embodiment 77 or 78, wherein the cell line does not express the FcγRIIIA receptor.

Embodiment 81

The cell line of any one of embodiments 77-80, wherein the cell line is a human cell line.

Embodiment 82

The cell line of any one of embodiments 77-81, wherein the cell line is a monocyte or macrophage cell line.

Embodiment 83

An assay method for determining a relative level of afucosylated antibodies, wherein the assay method includes contacting a test sample, or antibodies derived therefrom, with the cell line of embodiment 79 in the presence of a flavivirus, measuring the level of infection or virus output, and determining the level of afucosylated antibodies relative to the level of infection or virus output measured when a known level of afucosylated antibodies is contacted with the cell line in the presence of the flavivirus.

Embodiment 84

The assay method of embodiment 83, wherein antibodies derived from the test sample are contacted with the cell line, and said antibodies are IgG antibodies.

Embodiment 85

The assay method of embodiment 84, wherein the IgG antibodies comprise IgG1 antibodies.

Embodiment 86

The assay method of embodiment 84 or embodiment 85, wherein the IgG antibodies are IgG antibodies of all specificities.

Embodiment 87

The assay method of embodiment 84 or embodiment 85, wherein the IgG antibodies are IgG antibodies specific for a flaviviral antigen.

Embodiment 88

The assay method of embodiment 87, wherein the flaviviral antigen is a dengue viral antigen.

Embodiment 89

The assay method of embodiment 87, wherein the flaviviral antigen is a Zika viral antigen.

Embodiment 90

A pharmaceutical composition, the composition comprising fucosylated IgG antibodies, or fucosylated Fc regions thereof, wherein greater than 95 percent of the IgG antibodies, or Fc regions thereof, are fucosylated.

Embodiment 91

The pharmaceutical composition of embodiment 90, wherein the pharmaceutical formulation is formulated in a unit dosage form.

Embodiment 92

The pharmaceutical composition of embodiment 91, wherein the dose of IgG antibodies, or Fc regions thereof, is 0.1 mg/kg to 2.0 g/kg subject body weight for a subject having a body weight in the range of 50-100 kg.

Embodiment 93

The pharmaceutical composition of any one of embodiments 90-92, wherein the IgG antibodies are IgG1 antibodies.

Embodiment 94

The pharmaceutical composition of any one of embodiments 90-93, wherein the IgG antibodies are IgG antibodies of all specificities.

Embodiment 95

The pharmaceutical composition of any one of embodiments 90-93, wherein the IgG antibodies are IgG antibodies specific for a flaviviral antigen.

Embodiment 96

The pharmaceutical composition of embodiment 95, wherein the flaviviral antigen is a dengue viral antigen.

Embodiment 97

The pharmaceutical composition of embodiment 95, wherein the flaviviral antigen is a Zika viral antigen.

Embodiment 98

The pharmaceutical composition of any one of embodiments 95-97, wherein the IgG antibodies are flaviviral-neutalizing IgG antibodies.

Embodiment 99

A method of treating a subject acutely infected with a flavivirus and at risk of progression to clinically significant flaviviral infection or disease, the method including administering to the subject an inhibitor of FcγRT receptor signaling.

Embodiment 100

The method of embodiment 99, wherein the inhibitor includes an inhibitor of binding between the Fc region of IgG antibodies and the FcγRI receptor.

Embodiment 101

The method of any one of embodiments 99, wherein the inhibitor includes a nucleic acid inhibitor of expression of the FcγRT receptor.

Embodiment 102

A method of treating a subject acutely infected with a flavivirus and at risk of progression to clinically significant flaviviral infection or disease, the method including administering to the subject an inhibitor of immunoreceptor tyrosine-based activation motif (ITAM)-mediated signaling.

Embodiment 103

The method of embodiment 102, wherein the inhibitor includes an inhibitor of ITAM/nuclear factor of activated T cells (NFAT)-mediated signaling.

Embodiment 104

The method of embodiment 102, wherein the inhibitor includes an inhibitor of spleen tyrosine kinase (Syk).

Embodiment 105

The method of embodiment 102, wherein the inhibitor includes an inhibitor of NFAT.

Embodiment 106

The method of any one of embodiments 99-105, wherein the subject has tested positive for a flaviviral infection.

Embodiment 107

The method of any one of embodiments 99-106, wherein the subject has been determined to have an elevated level of afucosylated Fc glycans by assaying a biological sample from the subject.

Embodiment 108

The method of embodiment 107, wherein the IgG antibodies are IgG1 antibodies.

Embodiment 109

The method of embodiment 107 or embodiment 108, wherein the IgG antibodies are IgG antibodies of all specificities.

Embodiment 110

The method of embodiment 107 or embodiment 108, wherein the IgG antibodies are IgG antibodies specific for a flaviviral antigen.

Embodiment 111

The method of embodiment 110, wherein the flaviviral antigen is a dengue viral antigen.

Embodiment 112

The method of embodiment 110, wherein the flaviviral antigen is a Zika viral antigen.

Embodiment 113

The method of any one of embodiments 107-112, wherein the elevated level of afucosylated Fc glycans is defined as 5 percent or greater.

Embodiment 114

The method of embodiment 113, wherein the elevated level of afucosylated Fc glycans is defined as 10 percent or greater.

Embodiment 115

The method of any one of embodiments 99-114, wherein the subject is a human.

Embodiment 116

The method of embodiment 115, wherein the inhibitor of FcγRT receptor signaling includes a humanized antibody.

Embodiment 117

The method of embodiment 115, wherein the subject has the acute flaviviral infection in the presence of preexisting IgG antibodies that are reactive with the infecting flavivirus.

Embodiment 118

The method of embodiment 115, wherein the subject is an infant.

Embodiment 119

The method of embodiment 118, wherein the infant has a mother who has IgG antibodies that are reactive with the infecting flavivirus.

Embodiment 120

The method of any one of embodiments 107-119, wherein the biological sample is blood or a blood fraction.

Embodiment 121

The method of any one of embodiments 99-120, wherein said treating additionally includes hospitalizing the subject.

Embodiment 122

The method of any one of embodiments 99-121, wherein the flavivirus is a dengue virus, and the clinically significant flaviviral infection or disease includes severe dengue disease.

Embodiment 123

The method of embodiment 122, wherein said treating includes treatment to prevent or inhibit progression to, or to manage, severe dengue disease.

Embodiment 124

The method of embodiment 123, wherein said treating includes transfusion with blood and/or platelets.

Embodiment 125

An inhibitor of FcγRI, FcγRIIA, or FcγRIIIA, receptor signaling and/or of immunoreceptor tyrosine-based activation motif (ITAM)-mediated signaling for use in the method of any one of embodiments 50-76 or 99-124.

Embodiment 126

The inhibitor of embodiment 125, wherein the inhibitor is an inhibitor of FcγRI receptor signaling.

Embodiment 127

The inhibitor of embodiment 125, wherein the inhibitor is an inhibitor of FcγRIIA receptor signaling.

Embodiment 128

The inhibitor of embodiment 125, wherein the inhibitor is an inhibitor of FcγRIIIA receptor signaling.

Embodiment 129

The inhibitor of embodiment 125, wherein the inhibitor is an inhibitor of ITAM-mediated signaling.

BRIEF DESCRIPTION OF THE DRAWINGS

FIG. 5: Basic methods used for generating U937 cell lines.

FIG. 6A-6B: U937 Human monocyte cell lines. Expression of FcγRIIa (6A) and FcγRIIIa (6B) was confirmed by FACS. Deletion of FcγRIIa from FcγRIIa− cell lines was also confirmed by Sanger sequencing.

DETAILED DESCRIPTION

Definitions

Figure 1A:
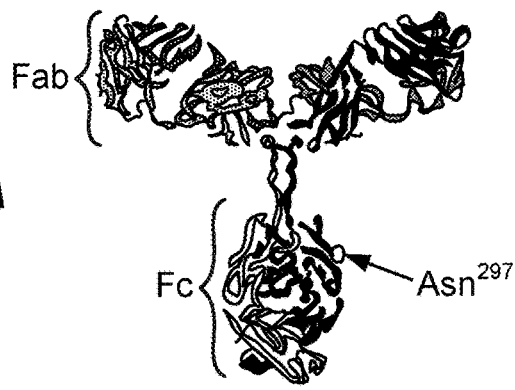
FIG. 1: IgG and the Fc glycan structure. (A) The Y-shaped structure of a human IgG1 antibody, with the protein backbone displayed in ribbon and space filling depiction of the glycan (red). The heavy and light chains combine to form the antigen-binding Fab portion, and the heavy chains extend to the Fc portion, which is responsible for initiating effector functions. (B) Composition of the core Fc glycan (boxed) can be modified by addition of specific saccharide units (fucose [F], N-acetylglucosamine [N], galactose [G], and sialic acids [S]) [3].
Figure 1B:
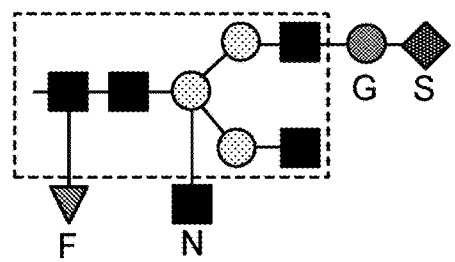
Figure 2:
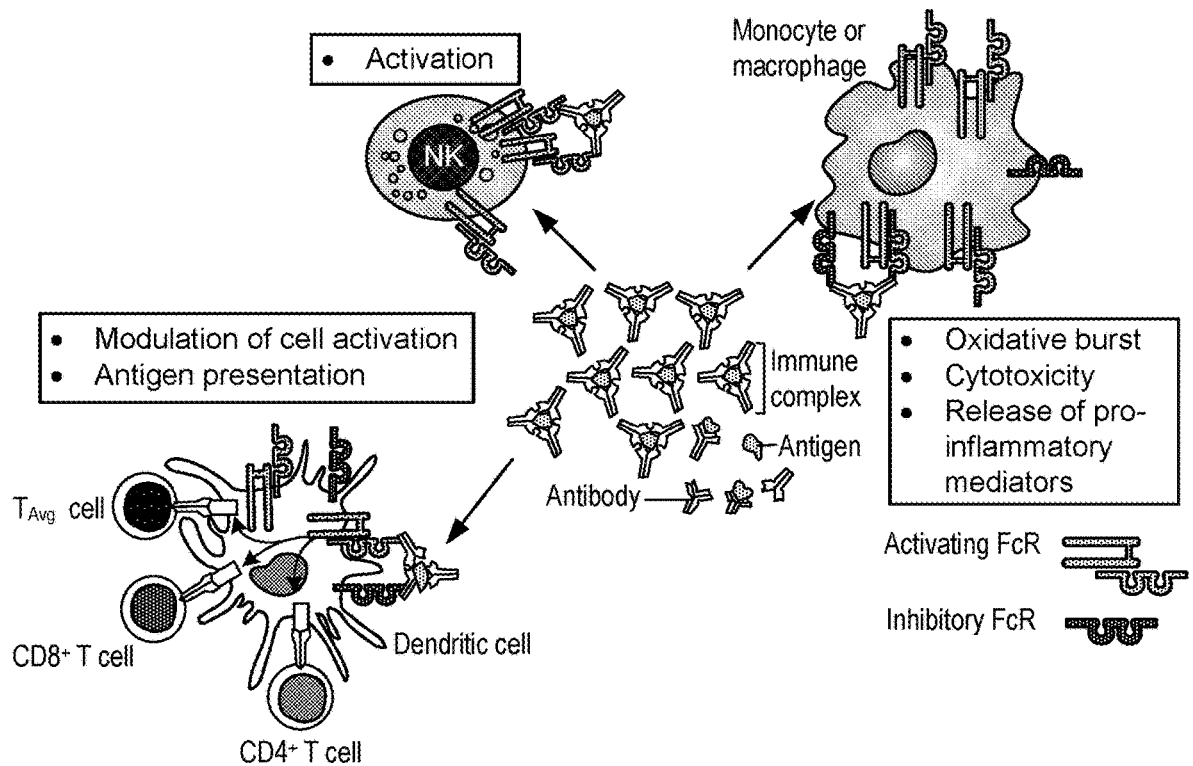
FIG. 2: Examples of modulation of cellular functions and activation by immune complexes.

Terms used in the claims and specification are defined as set forth below unless otherwise specified.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively.

A typical full-length (intact) immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments that can be produced, inter alia, by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes whole antibodies, antibody fragments either produced by the modification of whole antibodies or synthesized de novo using recombinant DNA methodologies. In certain embodiments antibodies include single chain antibodies (antibodies that exist as a single polypeptide chain), for example, single chain Fv antibodies (scFv) in which a variable heavy and a variable light chain are joined together (directly or through a peptide linker) to form a continuous polypeptide. In certain embodiments the single chain Fv antibody is a covalently linked $V_H$-$V_L$ heterodimer that may be expressed from a nucleic acid including $V_H$ and $V_L$ encoding sequences either joined directly or joined by a peptide-encoding linker (see, e.g., Huston, et al. (1988) Proc. Nat. Acad. Sci. USA, 85: 5879-5883). While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example, Fab molecules can be displayed on phage if one of the chains (heavy or light) is fused, for example, to g3 capsid protein and the complementary chain exported to the periplasm as a soluble molecule. The two chains can be encoded on the same or on different replicons. The important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). Accordingly, in certain embodiments, anti-Fc receptor antibodies include, but are not limited to all that have been displayed on phage or yeast (e.g., scFv, Fv, Fab and disulfide linked Fv (see, e.g., Reiter et al. (1995) Protein Eng. 8: 1323-1331)).

The term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are typically highly specific, being directed against a single epitope. In contrast to polyclonal antibody preparations which typically include different antibodies directed against different determinants (epitopes), each monoclonal antibody is directed against a single determinant on the antigen. The term "monoclonal" indicates the character of the antibody as being obtained from, or one of, a substantially homogeneous population of antibodies, and is not to be construed as requiring production of the antibody by any particular method. For example, monoclonal antibodies may be made by a variety of techniques, including, but not limited to, the hybridoma method (see, e.g., Kohler and Milstein. (1975) Nature, 256:495-497; Hongo et al. (1995) Hybridoma, 14 (3): 253-260; Harlow et al. (1988) Antibodies: A Laboratory Manual (Cold Spring Harbor Laboratory Press, 2d ed.); Hammerling et al. (1981) In: Monoclonal Antibodies and T-Cell Hybridomas 563-681 (Elsevier, N.Y.)), recombinant DNA methods (see, e.g., U.S. Pat. No. 4,816,567), phage-display technologies (see, e.g., Clackson et al. (1991) Nature, 352: 624-628; Marks et al. (1992) J. Mol. Biol. 222: 581-597; Sidhu et al. (2004) J. Mol. Biol. 338(2): 299-310; Lee et al. (2004) J. Mol. Biol. 340(5): 1073-1093; and the like), and technologies for producing human or human-like antibodies in animals that have parts or all of the human immunoglobulin loci or genes encoding human immunoglobulin sequences (see, e.g., PCT Patent Publication Nos: WO 1998/24893; WO 1996/34096; WO 1996/33735; and WO 1991/10741; U.S. Pat. Nos. 5,545,807; 5,545,806; 5,569,825; 5,625,126; 5,633,425; and U.S. Pat. No. 5,661,016; Jakobovits et al. (1993) Nature 362: 255-258; Bruggemann et al. (1993) Year in Immunol. 7: 33; Marks et al. (1992) Bio/Technology 10: 779-783; Lonberg et al. (1994) Nature 368: 856-859; Morrison (1994) Nature 368: 812-813; Fishwild et al. (1996) Nature Biotechnol. 14: 845-851); Neuberger (1996) Nature Biotechnol. 14: 826; Lonberg and Fluszar (1995) Intern. Rev. Immunol. 13: 65-93; and the like).

"Humanized antibodies" are forms of antibodies that contain sequence (typically minimal sequence) derived from non-human (e.g., murine) immunoglobulin the remaining sequence being derived from a human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or non-human primate having the desired specificity, affinity, and/or capacity. In some instances, framework residues of the human immunoglobulin are replaced by corresponding non-human residues. In certain embodiments. Humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more individual framework residue substitutions that improve antibody performance, such as binding affinity, isomerization, immunogenicity, and the like. The number of these amino acid substitutions in the framework is typically no more than 6 in the H chain, and in the L chain typically no more than 3. In certain embodiments the humanized antibody can also comprise at least a portion of an immunoglobulin constant region (Fc), typically that of a human immunoglobulin (see, e.g., Jones et al. (1986) Nature 321: 522-525; Riechmann et al. (1988) Nature 332: 323-329; Presta (1992) Curr. Op. Struct. Biol. 2: 593-596 (1992); Vaswani and Hamilton (1998) Ann. Allergy, Asthma. Immunol. 1: 105-115; Harris, (1995) Biochem. Soc. Transact. 23: 1035-1038; Hurle and Gross (1994) Curr. Op. Biotech. 5:428-433; and U.S. Pat. Nos. 6,982,321 and 7,087,409).

The term "Fc region" refers to a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include, but are not limited to, human IgG1, IgG2, IgG3 and IgG4.

An "Fc receptor" or "FcR" refers to a receptor that typically binds to an Fc region of an antibody. In certain embodiments the FcR is a native sequence human FcR. In certain embodiments the FcR is one that binds an IgG antibody (a gamma receptor) and includes, for example, receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain, (see, e.g., Daeron (1997) Annu. Rev. Immunol. 15: 203-234; Ravetch and Kinet (1991) Annu. Rev. Immunol. 9: 457-492 (1991); Capel et al. (1994) Immunometh. 4: 25-34; de Haas et al. (1995) J. Lab. Clin. Med. 126: 330-341). Other FcRs, including those to be identified in the future, are encompassed by the term "FcR" herein.

The terms "binding", "specific binding", and "specifically recognizes" are used interchangeably herein and indicates that an antibody exhibits substantial affinity for a specific molecule or fragment(s) thereof and is said to occur when the antibody is selective in that it does not exhibit significant cross-reactivity with other molecules lacking the target epitope. In certain embodiments substantial binding includes binding with a dissociation constant ($K_d$) of $10^{-6}$, $10^{-7}$, $10^{-8}$, $10^{-9}$, $10^{-10}$, $10^{-11}$, $10^{-12}$ M. or better. Values intermediate to those set forth herein are also contemplated, and preferred binding affinity can be indicated as a range of dissociation constants, for example preferred binding affinities for antibodies disclosed herein are represented by $K_d$ values ranging from $10^{-6}$ to $10^{-12}$M (i.e., micromolar to picomolar), preferably $10^{-7}$ to $10^{-12}$M, more preferably $10^{-7}$ to $10^{-12}$M or better. Binding affinity and selectivity can be determined using any art-recognized methods for determining such characteristics, including, for example, using Scatchard analysis and/or competitive (competition) binding assays (see, e.g., Wassaf et al. (2006) Anal. Biochem. 351(2):241-53; Epub 2006 Feb. 10 (BIACORE); and Murray and Brown (1999) J. Immunol. Meth. 127(1): 25-28 (ELISA)).

As used herein, the term "afucosylated Fc glycan" refers to Fc glycans lacking a core fucose on the Fc glycan of the IgG heavy chain.

As used herein, the phrase "determining the level of afucosylated Fc glycans in IgG antibodies" encompasses determining this level directly, by measuring afucosylated Fc glycans in IgG antibodies, or indirectly, by measuring fucosylated Fc glycans in IgG antibodies. For example, a level of afucosylated Fc glycans in IgG antibodies above 10% can be determined by measuring a level of fucosylated Fc glycans in IgG of less than 90%.

As used herein with reference to infection or disease, the term "clinically significant" refers to infection or disease requiring direct observation and/or treatment by a medical professional.

As used herein, the term "infant" refers to a child during the span of time from birth to 16 months.

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment which includes a delay in the onset or the prevention of the onset of a pathology or disease.

Figure 11:
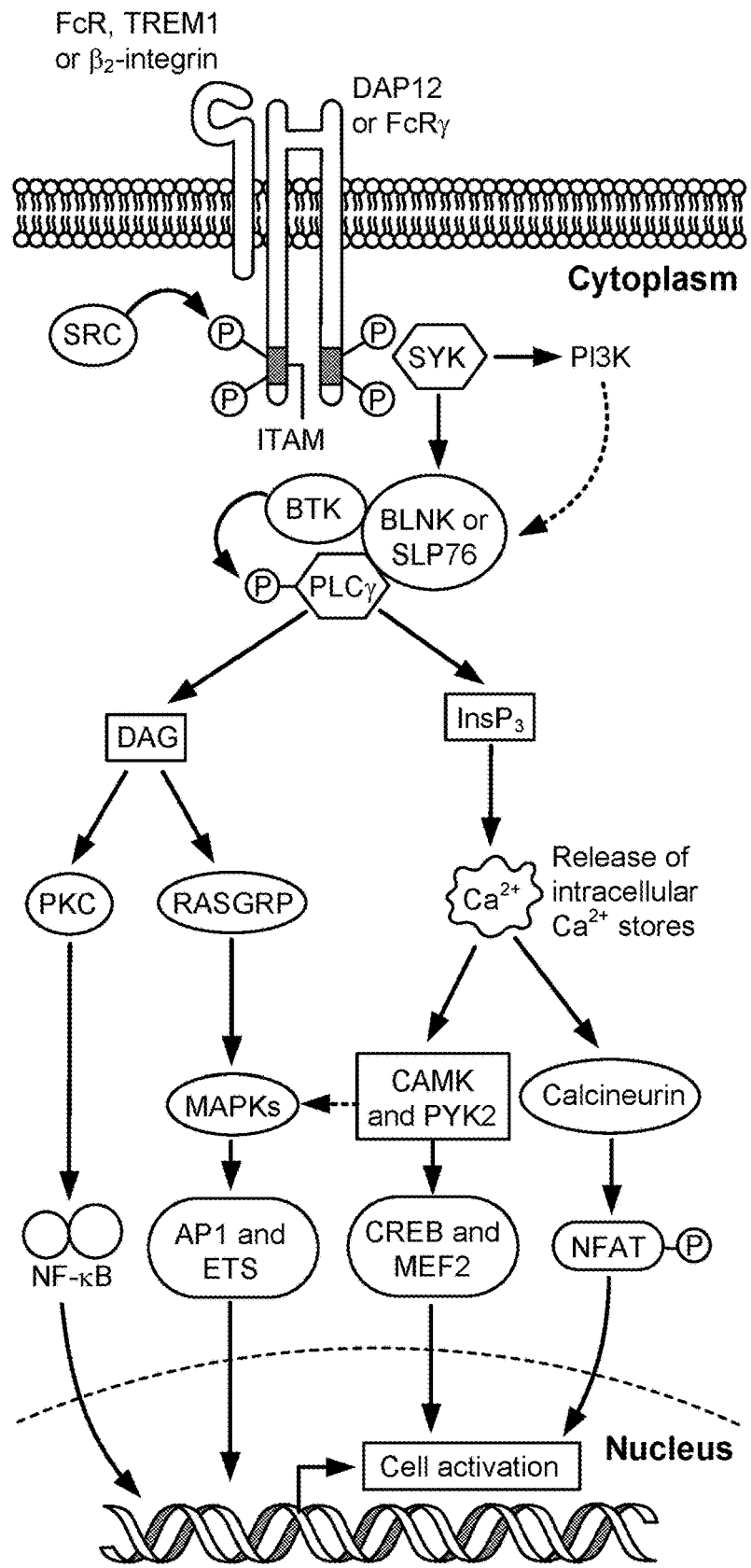
FIG. 11: ITAM-mediated signaling in myeloid cells. Crosslinking of immunoreceptor tyrosine-based activation motif (ITAM)-associated receptors (e.g., Fc receptors [FcRs]) leads to SRC-family kinase-dependent phosphorylation of tyrosines in the ITAM motif in the cytoplasmic domain of ITAM-containing adaptor molecules, followed by recruitment and activation of spleen tyrosine kinase (SYK). In myeloid cells, FcγRs and DAP12 are the major ITAM-containing adaptors, and SYK is the major recruited kinase. SYK initiates a signaling cascade that leads to the activation of Bruton's tyrosine kinase (BTK), the formation of multi-protein signaling complexes which is coordinated by the scaffolding adaptors B-cell linker (BLNK) and SRC-homology-2-domain-containing leukocyte protein of 76 kDa (SLP76) (which are partially redundant adaptors), and the activation of phospholipase Cγ (PLCγ). PLCγ activates key downstream effector pathways through the generation of the second messengers diacylglycerol (DAG) and inositol-1,4, 5-triphosphase (InsP$_3$) that activate the depicted kinase cascades, such as RAS guanyl-releasing protein (RASGRP), mitogen-activated protein kinases (MAPKs), calmodulin-dependent kinase (CAMK), and protein tyrosine kinase 2 (PYK2), calcineurin, and downstream transcription factors, such as nuclear factor-kappaB (NF-kB), activator protein 1 (AP1), and ETS, cyclic AMP-responsive element binding protein (CREB), myocyte enhancer factor 2 (MEF2) and nuclear factor of activated T cells (NFAT). Phosphoiniositide 3-kinase (PI3K); protein kinase C (PKC).

As used herein, the term "immunoreceptor tyrosine-based activation motif (ITAM)-mediated signaling" refers to the signaling pathway shown in FIG. 11. Individual components of this pathway are described above in the Brief Description of the Drawings.

As used herein, the term "an inhibitor of immunoreceptor tyrosine-based activation motif (ITAM)-mediated signaling" refers to any agent that inhibits the signaling activity of any post-receptor binding component of the ITAM-mediated signaling pathway.

As used herein, the term "ITAM/nuclear factor of activated T cells (NFAT)-mediated signaling" refers to the signaling pathway in FIG. 11 that leads to and includes the transcription factor NFAT.

As used herein, the term "an inhibitor of ITAM/NFAT-mediated signaling" refers to any agent that inhibits the signaling activity of any post-receptor binding component of the ITAM-mediated signaling pathway.

As used herein, the term "small molecule" refers to an organic compound having a molecular weight of less than about 900 daltons.

Antibody Analysis in Flaviviral Infection

Figure 3A:
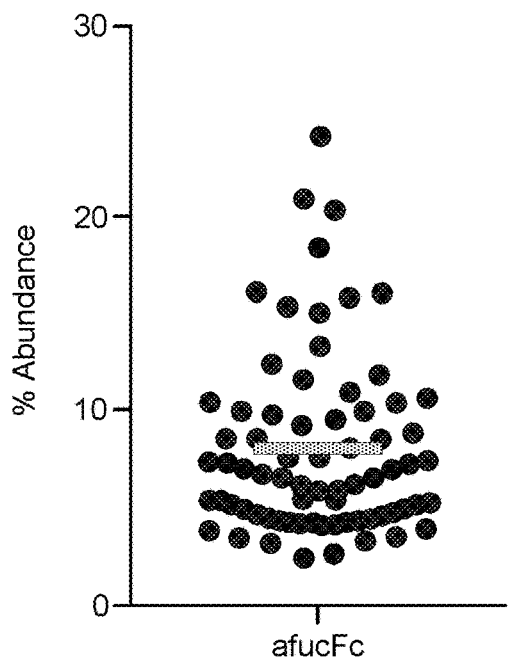
FIG. 3: Heterogeneity in structural determinants of Fc domains. Abundance of afucosylated Fc glycoforms (afucFc), sialylated gycoforms (Sfc), or the ratio of activating IgG1+IgG3 to inhibitory IgG2 subclass on anti-influenza hemagglutinin IgG from healthy adults.
Figure 3B:
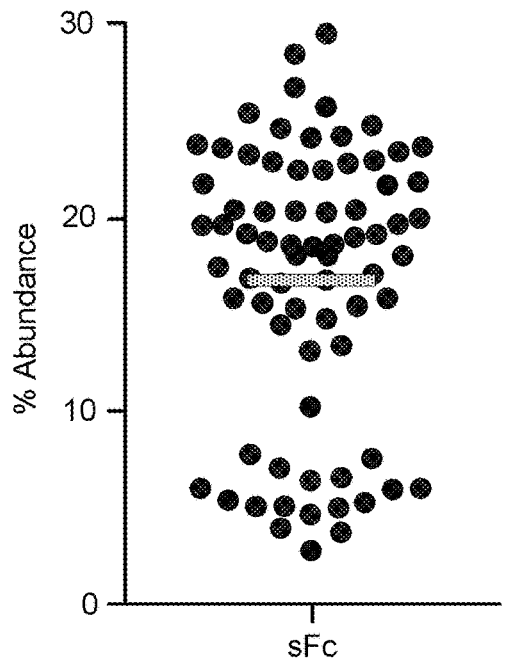
Figure 3C:
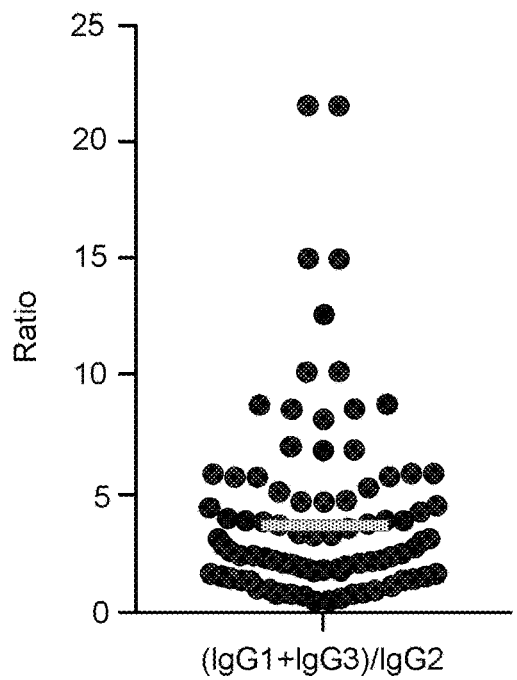

Humans have highly variable Fc domain repertoires, defined as the precise IgG subclass and Fc glycoform distributions of serum IgG. Indeed, the abundance of sialylated and afucosylated glycoforms on serum IgG can vary up to ~30% between individuals, while the ratio of the dominant activating to inhibitory IgG subclasses (IgG1/IgG2) varies by ~25% (FIG. 3). This heterogeneity in determinants of Fc-FcγR binding impacts FcγR signaling and thus modulates vaccine efficacy [3, 4], susceptibility to autoimmune disorders [5] and infectious diseases [2] and likely determines numerous additional antibody-mediated processes.

Afucosylated Fc glycans in IgG antibodies from individuals infected with a flavivirus correlate with progression to clinically significant, and often life-threatening disease. For example, afucosylated Fc glycans in IgG antibodies are believed to play a role in progression to severe dengue disease.

There are four serotypes of dengue virus (DENV) which are endemic in many regions of the world. DENV infections result in subclinical disease in nearly two-thirds of infections; the remaining infections range in clinical severity from mild, to classical dengue fever (DF), to the severe dengue hemorrhagic fever (DHF) and shock syndrome (DSS). The greatest risk factor for progression to DHF or DSS is the presence of reactive, non-neutralizing IgGs (RNNIgs). These antibodies bind to the infecting DENV and can mediate ADE of disease by increasing virus infection in Fc receptor (FcR)-bearing cells. Two circumstances place individuals at highest risk for progression to DHF/DSS due to the presence of RNNIgs: secondary infection with a distinct DENV serotype, and primary infection in infants of DENV-immune mothers.

Though the presence of RNNIgs is the major risk factor for progression to severe DENV disease, their presence alone does not predict disease progression. This suggests that only some IgG antibodies can trigger ADE of DENV infection. A study to determine whether individuals with severe secondary DENV infections have RNNIgs with a specific Fc domain repertoire established that, during acute secondary dengue infection, individuals with elevated afucosylated Fc glycans (afucFc) were at higher risk for progression to DHF/DSS and that these afucFc antibodies likely played a role in the pathogenesis of severe DENV disease (Wang, et al. (2017), IgG antibodies to dengue enhanced for FcγRIIIA binding determine disease severity, Science, 355 (6323):395-398, which is incorporated by reference herein for this description).

Accordingly, in some embodiments, a method of analyzing antibodies entails determining the level of afucosylated Fc glycans in IgG antibodies in a biological sample from a subject acutely infected with a flavivirus or from a maternal subject having an infant acutely infected with a flavivirus, wherein the subject has not been determined to have an autoimmune disorder.

Flaviviruses

Flavivirus is a genus of viruses in the family Flaviviridae. This genus includes the West Nile virus, dengue virus (DENV), tick-borne encephalitis virus, yellow fever virus, Zika virus and several other viruses which may cause encephalitis, as well as insect-specific flaviviruses (ISFs) such as cell fusing agent virus (CFAV), Palm Creek virus (PCV), and Parramatta River virus (PaRV).

Flaviviruses share several common aspects: common size (40-65 nm), symmetry (enveloped, icosahedral nucleocapsid), nucleic acid (positive-sense, single-stranded RNA around 10,000-11,000 bases), and appearance in the electron microscope.

Most of these viruses are transmitted by the bite from an infected arthropod (mosquito or tick) and hence, classified as arboviruses. Human infections with most of these arboviruses are incidental, as humans are unable to replicate the virus to high enough titers to reinfect the arthropods needed to continue the virus lifecycle—humans are then a dead end host. The exceptions to this are the yellow fever, dengue, and Zika viruses. These three viruses still require mosquito vectors, but are well-enough adapted to humans as to not necessarily depend upon animal hosts (although they continue to have important animal transmission routes, as well).

Other virus transmission routes for arboviruses include handling infected animal carcasses, blood transfusion, child birth and through consumption of unpasteurised milk products. Transmission from nonhuman vertebrates to humans without an intermediate vector arthropod is thought to be unlikely.

The known non-arboviruses of the flavivirus family reproduce in either arthropods or vertebrates, but not both, with one odd member of the genus affecting a nematode.

DENV and Zika viruses are closely enough related that antibodies generated against one cross-react with the other.

Subjects

The antibody analysis method can be employed using any subject capable of being infected by a flavivirus. In some embodiments, the subject is a mammal, more specifically, a primate, and even more specifically, a human.

In some embodiments, the subject is infected with a flavivirus, and in a variation of these embodiments, the infection is acute. The subject may be one that has tested positive for a flaviviral infection. In certain embodiments, the infection is a secondary infection. For example, the subject can have an acute flaviviral infection in the presence of preexisting IgG antibodies that are reactive with the infecting flavivirus.

In particular embodiments, the subject is an infant. In particular embodiments, the subject is the mother of an infant. In some embodiments where the subject is a mother, the infant is infected with a flavivirus, typically (though not necessarily) acutely. The infant may be one that has tested positive for a flaviviral infection. In a variation of these embodiments, the mother has, or had, at least one prior flavivirus infection. For example, a maternal subject can have IgG antibodies that are reactive with the same flavivirus infecting her infant.

Generally, when analyzing antibodies in connection with a flaviviral infection, the subject is one who has not been determined to have an autoimmune disorder. Because afucosylated antibodies also arise in autoimmune disorder, the same conclusions cannot necessarily be drawn from the detection of an elevated level of afucosylated antibodies in a subject with autoimmune disorder as in a subject not suffering from an autoimmune disorder.

Measurement of Afucosylated Fc glycans

Afucosylated Fc glycans can be measured by any convenient method, including that described in Wang, et al. (supra, which is incorporated by reference for this description). An illustrative method is given in Example 1.

In some embodiments, afucosylated Fc glycans can be measured using a novel cell line described below in the section entitled "Novel Cell Lines" and in Example 3. In particular, a test sample, or antibodies derived therefrom, can be contacted with a FcγRIIa-FcγRIIIa+ cell line (such as the FcγRIIa-FcγRIIIa+ U937 cells in Example 3) in the presence of a flavivirus, and the level of infection or virus output can be measured. This measurement can be compared to the level of infection or virus output measured when a known level of afucosylated antibodies (e.g., from a control sample that has a normal level of afucosylated antibodies) is contacted with the cell line in the presence of the flavivirus to determine a relative level of afucosylated antibodies. A level of infection or virus output of the test sample or test antibodies is greater than that of a control sample having a normally low level of afucosylated antibodies indicates that the test sample or test antibodies has a higher than normal level of afucosylated antibodies.

In some embodiments, an antibody that distinguishes between fucosylated and afucosylated Fc glycans can be employed in a standard immunoassay.

In some embodiments, the measurement is carried out on IgG1 antibodies. IgG antibodies for the measurement can be obtained from any biological sample reflecting the repertoire of IgG antibodies in the subject, typically blood or a blood fraction. Afucosylated Fc glycans can be measured in total IgG (i.e., all IgG antibodies in the sample) or in an IgG fraction. For example, IgG subclasses can be isolated using standard techniques, such as that described, for example, in Wang, et al. (supra, which is incorporated by reference for this description) or by Leblebici, et al. (2014), Separation of human immunoglobulin G subclasses on a protein A monolith column, J Chromatogr B Analyt Technol Biomed Life Sci., 962:89-93.

The IgG antibodies, whether all subclasses or just IgG1 can be IgG antibodies of all specificities. Alternatively, prior to measurement of afucosylated Fc glycans, antigen-specific antibodies can be isolated using any standard technique, such as affinity chromatography. In some embodiments, the IgG antibodies used for the measurement are IgG antibodies specific for a flaviviral antigen. For example, the IgG antibodies can be specific for a DENV envelope or NS1 protein antigen (from DENV serotype 1, 2, 3 or 4) or for a Zika envelope or NS1 viral antigen.

Figure 4:
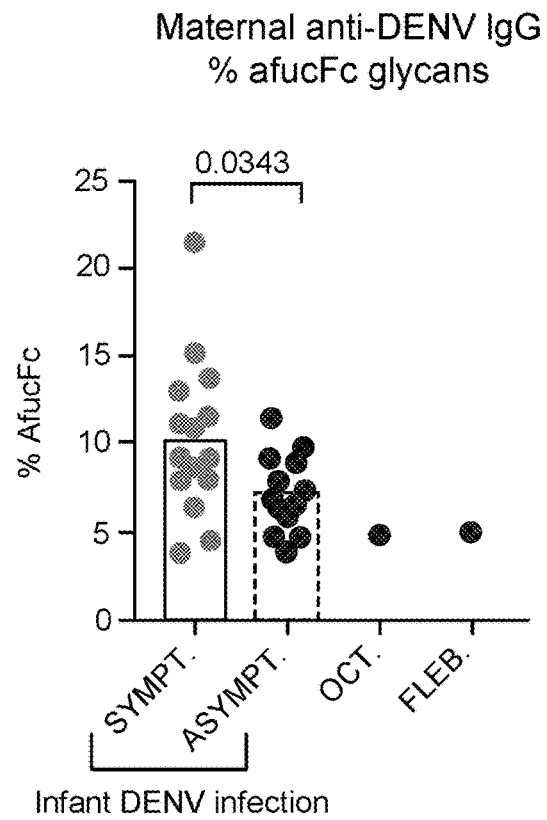
FIG. 4: Greater than 10% afucFc glycoforms on maternal IgG predicts symptomatic infant DENV infection. Levels of afucFc on maternal anti-DENV envelope IgG are shown. Greater than 10% abundance of afucFc on anti-DENV envelope IgG has a positive predictive value of 88.8% for symptomatic infant DENV disease. Symptomatic (Symp.), Asymptomatic (Asymp.), OCT. and FLEB. Are different commercial brands of IVIg.

In various embodiments, fucosylated Fc glycans are considered to be elevated when they make up at least 1, 2, 3, 4, 5, 6, 7, 8, 9, 11, 12, 13, 14, 15, 16, 17, 18, 19, 20, 21, 22, 23, 24, 25, 26, 27, 28, 29, or 30 percent of the IgG antibodies tested. The threshold for elevation is set, in a particular application, based on the desired predictive value of the test. For example, elevated maternal anti-DENV IgG (>10%) is a predictor of symptomatic infant DENV infection (Example 2, FIG. 4), with a predictive value of over 88% (PPV 88.8%). If the test antibodies are total IgG (e.g., all IgG subclasses and not antigen-specific), the threshold is, in some embodiments, set lower than if the test antibodies are antigen-specific).

Treatment of Flaviviral Infection Based on Antibody Analysis

A subject (including an infant) having at least one symptom of infection with a flavivirus and that has been determined to have an elevated level of afucosylated Fc glycans by assaying a biological sample from the subject is at increased risk for progression to clinically significant flaviviral infection and/or disease. Likewise, an infant having at least one symptom of infection with a flavivirus, whose mother has been determined to have an elevated level of afucosylated Fc glycans by assaying a biological sample from the mother, is at increased risk for progression to clinically significant flaviviral infection and/or disease. In some embodiments, the subject or the infant and/or mother will have tested positive for a flaviviral infection, such as DENV or Zika. Therefore, in some embodiments, the subject or infant is monitored for progression to clinically significant flaviviral infection or disease based on an elevated level of afucosylated Fc glycans in the biological sample from the subject or the infant's mother, respectively. In particular embodiments, the subject or infant is hospitalized.

In some embodiments, an afucosylated Fc glycan level of at least 5 percent (of, e.g., antigen-specific IgG) indicates that monitoring is in order. In some embodiments, this threshold is set a 10 percent.

In the case of DENV, clinically significant infection or disease can include severe dengue disease, sometimes diagnosed as dengue hemorrhagic fever (DHF) and/or shock syndrome (DSS). Early symptoms of DHF are similar to those of sub-clinical DENV. These include decreased appetite, fever, headache, joint and/or muscle aches, general malaise, vomiting. These symptoms are typically followed by restlessness and then worsening of the early symptoms, plus one or more of patches of blood under the skin, spots of blood on the skin, and a generalized rash. This phase can also include a shock-like state characterized by cold, clammy arms and legs and sweating (DSS). Physical exam may reveal: enlarged liver, low blood pressure, red eyes and/or throat, swollen glands, and a weak, rapid pulse.

Monitoring for progression to clinically significant infection or disease can include one or more of the following tests: arterial blood gases, blood tests, coagulation studied, electrolytes, hematocrit, liver enzymes, platelet count, serum studies, tourniquet test (to see whether blood patches form below the tourniquet), and chest X-ray (to detect build-up of fluid in the lungs and/or chest).

Treatment of clinically significant flaviviral infection or disease, such as severe dengue disease, can include, for example, one or more of: a blood or platelet transfusion to correct bleeding problems, intravenous fluids to treat dehydration, intravenous fluids and electrolytes to correct electrolyte imbalances, oxygen therapy to treat low blood oxygen, supportive care in an intensive care unit. Such measures can be taken to prevent or inhibit progression to, and/or to manage, clinically significant flaviviral infection or disease.

In some embodiments, treatment of clinically significant flaviviral infection or disease can include administering an inhibitor of FcγRIIA or FcγRIIIA receptor signaling. This intervention is based on the novel finding that these receptors play a role in progression to clinically significant infection or disease and is described further below in the section entitled "Inhibiting FcγRIIA or FcγRIIIA Receptor Signaling to Treat Infection and/or Reduce an Immune Response."

Vaccination Against Flaviviral Infection

The antibody analysis methods described herein are also useful in the context of vaccination against flaviviruses. Example 2 (below) establishes that it is the presence of preexisting afucosylated Fc glycans in IgG antibodies that indicates increased susceptibility to clinically significant flavivirus infection or disease. This means that in individuals having elevated afucosylated Fc glycans in their IgG antibodies, the risks associated with vaccination against a flavivirus can, in many cases, outweigh the benefits. Accordingly, measurement of elevated afucosylated Fc glycans in IgG antibodies provides a means of identifying individuals who should not be vaccinated.

A novel method of vaccinating against a flavivirus, thus, entails vaccinating a pre-selected patient population. In some embodiments, a subject pre-selected for a flaviviral vaccination is one that has been determined not to have an elevated level of afucosylated Fc glycans in IgG antibodies in a biological sample from the subject. In some embodiments, e.g., where the subject is an infant, if the mother of infant has been determined not to have an elevated level of afucosylated Fc glycans in IgG antibodies in a biological sample from the mother, the infant subject is pre-selected for a flaviviral vaccination. The antibody analysis in this context can be carried out essentially as described above.

In some embodiments, the measurement of elevated afucosylated Fc glycans among IgG that is specific for the flavivirus that is the target of the vaccine is the most predictive measurement. Example 2 shows, for instance, that the detection of afucosylated Fc glycans at a level of greater than 10% in dengue-reactive maternal IgG antibodies is highly predictive of susceptibility to severe dengue disease. Measurement of dengue- or Zika-reactive antibodies are of particular interest, especially in infants because of the serious consequences of clinically significant infection or disease (e.g., hemorrhagic fever and shock in the case of dengue and encephalitis, in the case of Zika).

Inhibiting FcγRI, FcγRIIA or FcγRIIIA Receptor Signaling to Treat Infection and/or Reduce an Immune Response Afucosylated Fc glycans increase affinity of IgGs for Fc receptors that activate immune responses. The novel finding that FcγRIIA or FcγRIIIA receptor signaling participates in infection and its enhancement in DENV infection (see Example 2) provides an additional therapeutic approach to treating flaviviral infection in the subject that is susceptible to developing clinically significant disease or infection. Of particular note, FcγRIIIa has, for the first time, been demonstrated to play a role in pathogenesis of DENV disease upon binding with an fucosylated Fc glycan. Because FcγRIIA or FcγRIIIA receptor are understood to be activating receptors generally, the work described herein indicates that inhibiting the binding of afucosylated Fc glycans to one or both of these receptors can be beneficial in other conditions in which afucosylated Fc glycans are present and an immune response plays a role in pathology. Examples of such conditions include autoimmune disorders, as described in Seeling, et. Al. (2017), Differential antibody glycosylation in autoimmunity: sweet biomarker or modulator of disease activity, Nature Reviews/Rheumatology, 13:621-630 (which is hereby incorporated by reference for this description).

Accordingly, in some embodiments, a method of treating a subject acutely infected with a flavivirus and at risk of progression to clinically significant flaviviral infection or disease can include an inhibitor of FcγRIIA or FcγRIIIA receptor signaling to the subject. Suitable subjects for this treatment method include those described above, especially those identified as susceptible to progression to clinically significant flaviviral infection or disease, e.g., based on elevated Fc glycans, e.g., using any of the methods described herein. In some embodiments, the subject is one that has been tested and found to have a flaviviral infection. In some embodiments, this approach to treatment is combined with monitoring or one or more of the other approaches to treatment described herein.

In some embodiments, a method of reducing an immune response in a subject in need thereof can include administering an inhibitor of FcγRIIIA receptor signaling to the subject. Suitable subjects for this treatment method include those described above, e.g., those who have elevated afucosylated Fc glycans along with one or more symptoms of a pathological immune response. Examples of suitable subjects include those who have one or more autoimmune disorders, such as, e.g., Addison disease, Celiac disease, Dermatomyositis, Graves disease, Hashimoto thyroiditis, Multiple sclerosis, Myasthenia gravis, Pernicious anemia, Sjogren syndrome, Systemic lupus erythematosus, Type 1 diabetes, or one of the other at least 80 autoimmune disorders that have been described.

Because both FcγRIIA and FcγRIIIA receptor signaling can play a role in the pathology of the conditions described above, the inhibitor administered to the subject can inhibit FcγRIIA, but not FcγRIIIA, and vice versa. Alternatively, the inhibitor can be one that inhibits signaling through both receptors, or two different inhibitors, one for FcγRIIA and one for FcγRIIIA can be co-administered. Any means for inhibiting receptor signaling that the subject can tolerate well can be employed in these methods, including, e.g., gene knockout, a nucleic acid inhibitor, a protein inhibitor, or a small-molecule inhibitor.

Inhibition of FcγRIIA and/or FcγRIIIA Receptor Signaling by Reducing the Level of Afucosylated Fc Glycans Pooled human serum IgGs have been used in the treatment of chronic inflammatory and autoimmune diseases (intravenous immunoglobulin; IVIG therapy) since the 1980s, when it was discovered that high doses (1-3 g/kg body weight) serum IgG preparations could be used to treat immunothrombocytompenia in children. A similar approach could be taken in treating in the treatment methods described herein, except that the therapeutic IgG antibodies administered have a higher level of fucosylated Fc regions than the biological sample from the subject. Without being bound by any particular theory, it is believed that adding fucosylated IgG antibodies to the subject's circulation effectively reduces the level of afucosylated IgGs, resulting in less signaling through FcγRIIA and/or FcγRIIIA Because the Fc glycan plays a role in in this immunomodulation, fucosylated Fc regions could, in some embodiments, be administered, rather than full IgGs. In some embodiments, the level of afucosylated Fc glycans in a subject's circulation can be lowered by obtaining IgG antibodies from the subject's circulation, treating these IgG antibodies exogenously to fucosulate them, and returning the fucosylated IgG antibodies to the subject's circulation.

Where the antigen(s) eliciting a pathological immune response are known, in some embodiments, the fucosylated IgG administered is specific for the antigen(s). When treating a subject infected with a flavivirus, anti-flavivirus IgG antibodies (i.e., specific for one or more flaviviral antigens) can be administered. In variations of such embodiments, one or more doses of fucosylated, neutralizing anti-flavivirus IgG can be administered. This latter approach is useful, for example, for treating an infant. In the infant, as the maternal neutralizing antibodies decay due to regular IgG half life, this is the time of risk for enhanced infant disease. Administering a dose of neutralizing IgG of high enough titer to outlast any afucosylated maternal IgG can reduce the risk of this disease enhancement. In some embodiments, fucosylated IgGs (or Fc regions) can be administered to a mother who's infant would be at high risk for disease during dengue infection or during acute dengue infection.

In general, when treating a subject with fucosylated IgG antibodies (or Fc regions thereof), the higher the level of fucosylated IgG antibodies in the preparation, the better. In various embodiments, the preparation has greater than 90, 91, 92, 93, 94, 95, 96, 97, 98, 99, or having 100 percent fucosylated antibodies. In various embodiments, IgG (or Fc region) dose is on the order of 0.1 mg/kg to 2 g/kg, 1.0 mg/kg to 1.75 g/kg, 1.0 mg/kg to 1.5 g/kg, 100 mg/kg to 1.25 g/kg, 500 mg/kg to 1.0 g/kg, or 750 mg/kg subject body weight.

Illustrative regimens for treating a subject with fucosylated IgG antibodies (or Fc regions thereof) include: 1, 2, or 3 times per day for a period of 1, 2, 3, 4, or 5 days.

Cell lines that produce IgG antibodies that are substantially all fucosylated in the Fc region are known and could be engineered to produce the desired IgG antibodies. For example, one or more broadly neutralizing anti-dengue and/or anti-Zika IgG antibodies could be expressed in a cell line such as HEK 239T cells.

Inhibition of Binding Between the Fc Region of IgG Antibodies and the FcγRIIA or FcγRIIIA Receptor In some embodiments, the inhibitor inhibits binding between the Fc region of IgG antibodies and the FcγRIIA or FcγRIIIA receptor. Example 3 describes the in vitro use of monoclonal antibodies against the FcγRIIA or FcγRIIIA receptor to elucidate the role of these receptors in dengue viral infection. This work demonstrates that, in some embodiments, an antibody can be used the binding inhibitor. Antibody inhibitors can be generated against the FcγRIIA or FcγRIIIA receptors, or antibodies that specifically bind afucosylated Fc regions can produced. When the subject is human, the inhibitor of FcγRIIA or FcγRIIIA receptor signaling can be a humanized antibody. Methods for producing therapeutic antibodies are well known to those of skill in the art.

Inhibition of Expression of the FcγRIIA or FcγRIIIA Receptor

Another approach to inhibiting signaling though the FcγRIIA and/or FcγRIIIA receptors is to down-regulate the expression of one or both of these receptors. Various standard techniques are available for reducing or blocking the expression of any gene whose sequence is known. These include, for example, genome editing techniques (such as CRISPR, as illustrated in Example 3), as well as oligonucleotide-based techniques like siRNA and antisense methods. For known nucleotide sequences, one of skill in the art can readily use any of these techniques to down-regulate expression or knock out the gene. The nucleotide sequences for multiple alleles and splice variants of these receptors are known. For example, FcγRIIa has 2 major alleles that are referred to as H131 and R131, and FcγRIIIa has 2 major alleles that are referred to as V158 and F158. Sequence information is publicly available, and examples are given below.

Inhibition of FcγRI Signaling

The above discussion of methods of inhibiting Fcγ receptor signaling also applies to inhibition of the FcγRI receptor, which also plays a role in flaviviral infection, as shown in Example 5.

Inhibition of ITAM-Mediated Signaling

All three of the Fcγ receptors discussed above activate the immunoreceptor tyrosine-based activation motif (ITAM)-mediated signaling pathway, which is shown in FIG. 11, and this pathway is implicated in flaviviral infection generally and in progression to clinically significant flaviviral infection or disease. In particular, Example 4 demonstrates that two components of this pathway, spleen tyrosine kinase (Syk) and nuclear transcription factor of activated T cells (NFAT), play a role in the signaling of these Fcγ receptors during flaviviral infection. Other illustrative components of the pathway from Syk to NFAT that represent targets for flaviviral therapies include: Bruton's tyrosine kinase (BTK), B-cell linker (BLNK), SRC-homology-2-domain-containing leukocyte protein of 76 kDa (SLP76), phospholipase Cγ (PLCγ), and calcineurin.

Types of Inhibitors

The methods described herein can employ any type of inhibitor that can be administered to a subject, including, e.g., nucleic acids, polyclonal or monoclonal antibodies, antibody fragments that include the Fc region, antibody variants (e.g., humanized antibodies), as well as peptides, peptide analogs, and small molecules.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al, 1987, *J. Med. Chem.* 30:1229, which are incorporated herein by reference for their descriptions of peptide mimetics. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH$_2$—NH—, —CH$_2$—S—, —CH$_2$—CH$_2$—, —CH=CH—(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

Small-molecule inhibitors are available for Bruton's tyrosine kinase (BTK), B-cell linker (BLNK), phospholipase Cγ (PLCγ), calcineurin, and NFAT, in addition to Syk (see Example 4). BTK inhibitors include, for example, ibrutinib (PCI-32765), acalabrutinib, ONO-4059, spebrutinib (AVL-292, CC-292), BGB-3111, and HM71224. Phospholipase C inhibitors include aminosteroid (U73122), and edelfosine (ET-18OCH3). Calcineurin inhibitors include, for example, ciclosporin, voclosporin, pimecrolimus and tacrolimus.

```
mRNA sequence for the Homo sapiens Fc fragment of IgG receptor
IIa (FCGR2A), transcript variant 1:
NCBI Reference Sequence: NM_001136219.1
(SEQ ID NO: 1)
   1 ctcttttcta agcttgtctc ttaaaaccca ctggacgttg gcacagtgct gggatgacta 61 tggagaccca aatgtctcag aatgtatgtc ccagaaacct gtggctgctt caaccattga 121 cagttttgct gctgctggct tctgcagaca gtcaagctgc agctccccca aaggctgtgc 181 tgaaacttga gccccgtgg atcaacgtgc tccaggagga ctctgtgact ctgacatgcc 241 aggggctcg cagccctgag agcgactcca ttcagtggtt ccacaatggg aatctcattc 301 ccacccacac gcagcccagc tacaggttca aggccaacaa caatgacagc ggggagtaca 361 cgtgccagac tggccagacc agcctcagcg accctgtgca tctgactgtg ctttccgaat 421 ggctggtgct ccagacccct cacctggagt tccaggaggg agaaaccatc atgctgaggt 481 gccacagctg gaaggacaag cctctggtca aggtcacatt cttccagaat ggaaaatccc 541 agaaattctc ccatttggat cccaccttct ccatcccaca agcaaaccac agtcacagtg 601 gtgattacca ctgcacagga aacataggct acacgctgtt ctcatccaag cctgtgacca 661 tcactgtcca agtgcccagc atgggcagct cttcaccaat ggggatcatt gtggctgtgg 721 tcattgcgac tgctgtagca gccattgttg ctgctgtagt ggccttgatc tactgcagga 781 aaaagcggat ttcagccaat tccactgatc ctgtgaaggc tgcccaattt gagccacctg 841 gacgtcaaat gattgccatc agaaagagac aacttgaaga aaccaacaat gactatgaaa 901 cagctgacgg cggctacatg actctgaacc ccagggcacc tactgacgat gataaaaaca 961 tctacctgac tcttcctccc aacgaccatg tcaacagtaa taactaaaga gtaacgttat 1021 gccatgtggt catactctca gcttgctgag tggatgacaa aaagagggga attgttaaag 1081 gaaaatttaa atggagactg gaaaaatcct gagcaaacaa aaccacctgg cccttagaaa 1141 tagcttttaac tttgcttaaa ctacaaacac aagcaaaact tcacggggtc atactacata 1201 caagcataag caaaacttaa cttggatcat ttctggtaaa tgcttatgtt agaaataaga 1261 caacccagc caatcacaag cagcctacta acatataatt aggtgactag ggactttcta 1321 agaagatacc taccccccaaa aaacaattat gtaattgaaa accaaccgat tgcctttatt 1381 ttgcttccac attttcccaa taaatacttg cctgtgacat tttgccactg gaacactaaa 1441 cttcatgaat tgcgcctcag atttttcctt taacatcttt ttttttttg acagagtctc 1501 aatctgttac ccaggctgga gtgcagtggt gctatcttgg ctcactgcaa acccgcctcc
```

-continued

```
1561 caggtttaag cgattctcat gcctcagcct cccagtagct gggattagag gcatgtgcca 1621 tcatacccag ctaattttg tattttttat ttttttttt tagtagagac agggtttcgc 1681 aatgttggcc aggccgatct cgaacttctg gcctctagcg atctgcccgc ctcggcctcc 1741 caaagtgctg ggatgaccag catcagcccc aatgtccagc ctctttaaca tcttctttcc 1801 tatgccctct ctgtggatcc ctactgctgg tttctgcctt ctccatgctg agaacaaaat 1861 cacctattca ctgcttatgc agtcggaagc tccagaagaa caaagagccc aattaccaga 1921 accacattaa gtctccattg ttttgccttg ggatttgaga agagaattag agaggtgagg 1981 atctggtatt tcctggacta aattcccctt ggggaagacg aagggatgct gcagttccaa 2041 aagagaagga ctcttccaga gtcatctacc tgagtcccaa agctccctgt cctgaaagcc 2101 acagacaata tggtcccaaa tgactgactg caccttctgt gcctcagccg ttcttgacat 2161 caagaatctt ctgttccaca tccacacagc caatacaatt agtcaaacca ctgttattaa 2221 cagatgtagc aacatgagaa acgcttatgt tacaggttac atgagagcaa tcatgtaagt 2281 ctatatgact tcagaaatgt taaaatagac taacctctaa caacaaatta aaagtgattg 2341 tttcaaggtg atgcaattat tgatgaccta ttttattttt ctataatgat catatattac 2401 ctttgtaata aaacattata accaaaaaca
```

DNA sequence for Homo sapiens Fc fragment of IgG receptor IIIa
(FCGR3A), RefSeqGene (LRG_60) on chromosome 1:
NCBI Reference Sequence: NG_009066.1 (SEQ ID NO: 2)
>NG_009066.1:5001-13865 Homo sapiens Fc fragment of IgG receptor IIIa
(FCGR3A), RefSeqGene (LRG_60) on chromosome 1

```
GGAGCCCCGGCTCCTAGGCTGACAGACCAGCCCAGATCCAGTGGCCGGAGGGGCCTGAGCTAAATCCGC
AGGACCTGGGTAACACGAGGAAGGTAAAGAGTTCCTGTCCTCGCCCCTCCCCACCCCCACCTTTTCTGTG
ATCTTTTCAGCCTTTCGCTGGTGACTTGTTCTTCCAGGGCCCATTTCTCTACCCTACCTGGGTTTCTTCT
AACCTGGAAATCTAATGATCAAATCACACTAAAAAGTCAGTAGCTCCTGTGGATTACATATCCCAGGAGC
ATATAGATTTTGAATTTTGAATTTTGAAAGAAATTCTGCGTGGAGATAATATTGAGGCAGAGACACTGCT
AGTGGTCTGAAGATTTGAAAGGACCACTTTCTGTGTGCAGGCAGGGCCTCAGCTGGAGATAGATGGGTCT
GGGCGAGGCAGGAGAGTGACAAGTTCTGAGGTGAAATGAAGGAAGCCCTCAGAGAATGCTCCTCCCACCT
TGAATCTCATCCCCAGGGTCTCACTGTCCCATTCTTGGTGCTGGGTGGATCCAAATCCAGGAGATGGGGC
AAGCATCCTGGGATGGCTGAGGGCACACTCTGGCAGATTCTGTGTGTGTCCTCAGATGCTCAGCCACAGA
CCTTTGAGGGAGTAAAGGGGGCAGACCCACCCACCCTTGCCTCCAGGCTCTTTCCTTCCTGGTCCTGTTCT
ATGGTGGGGCTCCCTTGCCAGACTTCAGACTGAGAAGTCAGATGAAGTTTCAAGAAAAGGAAATTGGTGG
GTGACAGAGATGGGTGGAGGGGCTGGGGAAAGGCTGTTTACTTCCTCCTGTCTAGTCGGTTTGGTCCCTT
TAGGGCTCCGGATATCTTTGGTGACTTGTCCACTCCAGTGTGGCATCATGTGGCAGCTGCTCCTCCCAAC
TGCTCTGCTACTTCTAGGTAAGTCAGGGTCTCCCTGGTTGAGGGAGAAGTTTGAGATGCCTTGGGTTCAG
CAGAGACCCCTTTTCAGGCTACGAATGAGACTCCCACGAAGGGATGGGACCCCTCACCACATCTATAGCT
GTGGATTGAGCTCCTAGGACAAGCCAAGATGGGGCTAGAAATGAGGAGAATGCTGGTTCCAATTGGGGCA
TACTCATGAGTGAGGCCAGTCACTTCACCCCTCTGGGTCCCAGAATCACTCTGTGGAACCAAAGAGCTTC
GACTAGATGGTCCCTAGGGTCTGTCTCTTTCAGTTTGACATTCCAGGGTTCTCCTCTATGATTTTCAATT
TCTACCCTTTCTTGTGGGGATATGGGTTGAGGCTCTTTCTGTAGCTTGGTTCAGGGAAATTCAACCTGTA
CCCTTAATTTGTGAGTTTGCACAGGGAGCAAGGGTAAGGGAGCAGTGTTGAAAATAGGGATTTGTGTTG
ACAGTGGCGCAAGAGGCATGAACAGTGGAGACCAGAGAGCAGGTAGCAAGGTTTCCACCAGAAACATCCT
GATTCTTGGGAAAATTGGGCTCCTGGGGCAGAGGAGGGCAGGGGAGTTTTAAACTCACTCTATGTTCTAA
TCACTCTGATCTCTGCCCCTACTCAATATTTGATTTATCTTTTTTCTTGCAGTTTCAGCTGGCATGCGGA
```

-continued

```
CTGGTGAGTCAGCTTCATGGTCTTGGATTGACCCAGTGGGGCACATATGGGACAAAGGCCATAAGATAT

TGGGAAATGCTTGTTGAATGGGAAAATGCTGATGTGGGGTTAGCAGGGATAGTTCCTCCAACACAGCAGA

ACTTGGCCCTGTGCTTCTCTGGCCAGCTTTCCTTAAGATACTGAACAGGCCAAAAATGGGGCCAAGATGC

TCTAAGACTGAGCCACCAAGCATGGGTTTGCAATGAGCTCATTCTGGCTTTGAGGCTCCCTGGGAATGGC

AGTGTAGAGCCTGCTCCTCTCCCTGTCCTCACCCCACATTATCTTGGCTCCTCAGAAGATCTCCCAAAGG

CTGTGGTGTTCCTGGAGCCTCAATGGTACAGGGTGCTCGAGAAGGACAGTGTGACTCTGAAGTGCCAGGG

AGCCTACTCCCCTGAGGACAATTCCACACAGTGGTTTCACAATGAGAGCCTCATCTCAAGCCAGGCCTCG

AGCTACTTCATTGACGCTGCCACAGTCGACGACAGTGGAGAGTACAGGTGCCAGACAAACCTCTCCACCC

TCAGTGACCCGGTGCAGCTAGAAGTCCATATCGGTGAGTTGATGAAGGGGAAGAGGAAAATCACCAATAA

AGGGTGAAACAAAGGGTCCTGAAATACTTGGTAAGAGCCAGAGATGATATTCTTAGAGATAAAAGCTAAG

ATGAGATGATGTGTGGTCCCACTGAATGGTATCAGAGTTGTAGTCCTAGCTCTAAGTAGGTCTTGGGCAA

AATGTCAAAGCCTGTCAGACAGTAGATATAGGACTGCTGCATTGCACAATTCCAAGAATCCCCATATGGA

GTGCATACAATGTGAATGTGTCATGTGAAGGTTAGGCCATGGCATAGATGCTCAATAATAGTTATTTATA

TATTTATTTTCATTTTTTTTAATTTTATTTTTTGAGACAGAGTATCACTCTGTCACCCAGGCTGGAGTGC

AATGCGGCAATCTCAGCTCACTGCAACTTCTGCCCCCTTGGGTTGTAGTGATTCTCCTGCCTCAGCCTCC

CGAGTAGCTGAGATTACAGGCACCCGCCACCACGCCCAGCTAATTTTTGTATTTTTAGTAGAGACAGGGT

TTCACCATGTTGGTCAGTCTGGTCTCAAACTCCTGACCTCAGGTGATTCACCAGCCTTGGCTTCCCAAAG

TGCTGGGACTACAGGCGTGAGCCACCACACCTGGCCAATAATATTTATTGAATAAATTAATGAATTTGGT

GTTAGGACCTCAATCTCCTTCTCGCTCTCAGACATGTAATGCCCTAAGCCACCTCCCAAAGCAATCCTAG

TGGCCTAGCATCATATCTTTCTGTCTCCTCATCAATGCTATACTCAAACCTATAATTAAGCATAAATTTG

GTAATGTGATAGCTCTTCCAATAGAGGCAGATACATGTTCAGCCTGCACATTAATCATGACATGAAAGTT

CTTGTGTACTATTAACAGAATATAGACGTCAGACACAGGTAGGAGAAATATTTTGAAGGCAGAGGTCTTT

CCTGGTGTCCCTACAATCTTACCACATAGGCTGGTCCCTGCAGTGTCGCCCTGCAAACCTAACTCTACTT

CCACGGCTGTTCCATTCATACAATGTTTATGGGTGGAACAAGCTTTGGGGGAAGAAGGGCATAAGGAGGT

GGATCTGCAAGAGAGCTCCATGGAATTGGGCCTCTGAAACTGATTTTTGTGGCTCTTTGGCCTCTGACAG

TACCACTCAACTGACATGGTCTTCACTCTCCAGAGCTACAAGAAGATATGTCCATTTCTAGCTAGGTAAG

AGATGTCCACCTACAACCAAATAAATGGGGAATTACCAAGAGAAAGCAATAGAAAAATCAAGTCTAAG

AGTTACTAGTTTGCCTTGAACTTGGCTCTAGAAACTGGCTTTAGAAGTCTAGCCAATCAAGGCTATATTA

AACTGTGACCATGAGAATTAGCTTCACCAGGTAAACTTCTGAGCATCCTTTAATCCTTTAGGACCCATTT

CACTTATGTCCTCCTCTGAGAAGCATTTTTACTTCTTTTTTTGTTTGTTTGTTTGTTTGTTTTGTT

TTTGTTTTTGAGACAGAGTCTCTCTCTGTCACCCAAGCTGGAGTGCAGTGGCGCAATCTTGGCTCACTGC

AACCTCCACCTCCCGGGTTCAAGCAATTCTCCTGCCTCAGCCTCCCAAGTAGCTGGGACTACAGGTGCAT

GCCACCACGCCCGGCTAATTTTTTGTATTTTTAGTAGAGACAGGGTTTCGCAGCGTTAGCCAGGATGGTC

TTGATCTCCTGACTTCATGATCTGCCCACCTCGGCCTCCCAAAGTACTAGGATTACAGATGTGAGCCACC

GCGCCCAGCCTGCATTTTTTACTTCTTTCAGGCAGAATTTCTTTATTCCAATCTAGTCAGCCCCGCAGTC

CTTTATTCTTAGCCTGTTGTAGCACTTGTCATATTGTATTGTGATTATTTCTGAATATTTATGTTTCTAT

GTCTAGACTGTAGATTCTTTGAGGCTGAGAACTATATGTCCCATCATCTGGGTATCTCCAGTCCACAGTG

TGTCATACATAGTGAGTGCTTGATGAAATATCACTTGAAGGAATATACATATGGACATTCACTGGGTCCA

TGACAGGATAGATTCGAACAAGAATGTTCCTCCAAAGGCCACCAGACTATATACTAACCATGACTTTATG

CTAATAATGATTCATCTCTCTGCTGAAAAAGTAAGTGGATAGATAGGCACATGGCTTCTTTTGATAAATG

ATATCTCTTAATAGGTAATGAAGATTACTTTCTGTTTGGCAAATCTTTGTGGTAGAGAATCATGACCAAC
```

-continued

```
ACACGTCCTACCAATTTTGTTTAGCATCAGGTAGTAGATTTTTTAAATTATAGTAATTCAAGCTGAGAAT
GTAGATTTAAAAAATAAAATTATTGTAAATTTTGTTTTGTTCTTATTACAAAAGTCATTTGGGGTCAATT
TCAAAAATATATAAAAGTAAACAGGAGAAATTTAAAATGTCCTTCAGTCCCACTCCTTCAGAGAAAACCC
CTGTTAATATGTAAGTGCATATCCTTCTTTTTTCTGTGCATAATACTTTTTAAAATATTTGAAGTATTAT
GCTTTTTTAACTTAAAATTGTCTCATGAATATTTTCTTATGCCATTATAATACTTACCTATAACATCATT
ATTTTTTAATTATTCAGGCCCTTTCCCGACCATGACCTCATGTTCTCTCTTTGTGAAGTCTGATTACTTG
GTGACATGATCGTGAGAATAAGCTCTGGCGATATAAGAATTTCCTCTCTTGAAGGCCATGCTCAGTAAAT
TACTTGGTGACATGATCGTGAGAATAAGCTCTGGCGATACAAGAATTTCCTCTCTTGAAGGCCATGCTCA
GTAATAAAGTTGGTCTCACCGAGGCCCTGTGACACCTTAGAAACCACGAATTGCCAGGCTGAGCAATACC
AGTCCCGCCCTTCCCCTCCCTGGTGTTTACATTGAGTTCTCCTTCACAATTTCTGCAGCCACTCCGTGGC
CACCGTCACCTTATTCCTGACTGCCACAAGAGTCTTTCAATATTCCTTTGATTGCCTATTCCTTCTGAAA
TCTACCTTTTCCTCTAATAGGGCAATTCATCATTTTCAAATGCAATTTTTACTCTGATCTAGAACTTACT
GTGAATCCTTGTCACCTGCCACAGCAAATCTAAGTCTAGCACTTAAGGATCCTGCAGATATGCTCATCGT
TGCTTCTCACTTACCTCATTGCTTAGTCCCTCTGCTCTAACCCTGTGTGTTGATCACATGTGTGTGTGTC
CCTCTTCCCCATTAGACAAAGGTCTTGGTATGACTTCAGTTCTCTTGCAGGGCCCCATCAGCTCTTCCCC
AAAGGGAGCTATGCAGGGTTGACTCCCAATCTGGCTTTCCCTTATGTCTCAGGATCTGGGTGGTACGTGG
CCCCTTCACAAAGCTCTGCACTGAGAGCTGAGGCCTCCCGGGCCTGGGGTGTCTGTGTCTTTCAGGCTGG
CTGTTGCTCCAGGCCCCTCGGTGGGTGTTCAAGGAGGAAGACCCTATTCACCTGAGGTGTCACAGCTGGA
AGAACACTGCTCTGCATAAGGTCACATATTTACAGAATGGCAAAGGCAGGAAGTATTTTCATCATAATTC
TGACTTCTACATTCCAAAAGCCACACTCAAAGACAGCGGCTCCTACTTCTGCAGGGGGCTTTTTGGGAGT
AAAAATGTGTCTTCAGAGACTGTGAACATCACCATCACTCAAGGTGAGACATGTGCCACCCTGGAATGCC
CAGGGACGCCTGTGTGTGGAACCTGCAATCACACTGGGAAGTTGAGTTGGGAGGAGATTCCTGATTCTTA
CACGCACTTCTTCATATGTGGTTCCCTCCTGGTGATCACCAGGAGGTCCCCAAAAGTCCCTGATTGCAGG
GTAGGTTTGCAGCTCTGTTTCAGTCCATTCTTTTGGGGTAGCTAGGAGGTGTCATTCACTCTGCAGCATG
ATGGCAGGAGCAGAAGCCACATCTCCTCCCCAATAAATACCTCTGTCTTTCCTTACGCTAATCACACCCA
CGGTGTCATATGTTCCTATCGTGCTGGCCTCCTTCTTATCCAAGCCTTTTAGCCACGATCCAAACTGGCA
GGAGCCCCTCATCCCCTCACAGAAAGAGCCCAGAACCTGGGTTCTGGCCCTGCAGCTAATTAACCATCTG
ACCAGAGGTGAGCCACTTAGTCTCTCTGAACCCCAATTTCTTCTTCCGTAACAAAAATAAGCTGACATTT
ATTGGGCACCTTTCAGTGTGCTAGACTCTGTGCTAAACAATTCTTTACATGCACCTGGTTTGACTATCAC
AGTAGACCTTCACAACATGAGATAGGTAATATTCCATTTTACAGATGAAGTAACCGAGGTGCAAAAATAA
ATAAATAAGTTTCCCTAAGGTCACATCAAAGACTTCAAAGCCTGTATATTTAACCAGTAAGTAAAAGATT
TGAACAAGCACTAATATCCTATGATCCCATTAAGTCATCCACAAAACATCTCTAGGTTCTGTAGCACCAG
CCTCCAGAATCAGAGCTCTAGAGTGGTGTGCCTGGACTTTCCAGTTTCACAGAACTTCTATCTGTAACTA
GCCCAAGACATAAATTGTAAACAATTTGCATGTAGAAAGGCAGCAAAACACCTTTTGAGATTTTGACACT
ACAATGCCATAATTTGTACAAAAATAATTTCATGACACTTTAAACTGAAAGTAAATACTCCCAAGTGGTT
AGGGAAAGAGAGCAAATAAAGCAAATGGGTAACATGTAAACAATGAGTGGATCTGGGTAAAGGATATAC
GAGATTAAACTATTCTGGTCATTTTTTTTTAAGTTTGGAAATATATCAAAATCAAGAGTTTAAAAAATT
GAAATGCAAAATCAACAAATTTGTCCCAGTTTCTAGACCATAGCATTGTCTGACAATTTCTTAACTGTCA
CACAAAACCCAGCTTACAACCTAACTTGTTAACGCTCCCTGTCACATCTCTGTCAAACAAGCAGGAGCCT
TTGCTCAGTGTTTGGTGAGCTGTCCTCTGCTCAGATAGCACTAAGATCAGGAACCAATGGGAGGAAGCAA
```

-continued
```
TACTTTCCCCCAGACTTCCCCACCATTCCTACCACTTGCCTGTTGGCTGTTGTCAAAGACTTTCTACTGG

TGACCTCACTGTTTGTTCCAAATATCTGCCTTAGTGACTGTCATTTTTTTTCATCTCTCCACTTCTCCTA

ATAGGTTTGGCAGTGTCAACCATCTCATCATTCTTTCCACCTGGGTACCAAGTCTCTTTCTGCTTGGTGA

TGGTACTCCTTTTTGCAGTGGACACAGGACTATATTTCTCTGTGAAGACAAACATTCGAAGCTCAACAAG

AGACTGGAAGGACCATAAATTTAAATGGAGAAAGGACCCTCAAGACAAATGACCCCCATCCCATGGGGT

AATAAGAGCAGTAGCAGCAGCATCTCTGAACATTTCTCTGGATTTGCAACCCCATCATCCTCAGGCCTCT

CTACAAGCAGCAGGAAACATAGAACTCAGAGCCAGATCCCTTATCCAACTCTCGACTTTTCCTTGGTCTC

CAGTGGAAGGGAAAAGCCCATGATCTTCAAGCAGGGAAGCCCCAGTGAGTAGCTGCATTCCTAGAAATTG

AAGTTTCAGAGCTACACAAACACTTTTTCTGTCCCAACCGTTCCCTCACAGCAAAGCAACAATACAGGCT

AGGGATGGTAATCCTTTAAACATACAAAAATTGCTCGTGTTATAAATTACCCAGTTTAGAGGGGAAAAAA

AAACAATTATTCCTAAATAAATGGATAAGTAGAATTAATGGTTGAGGCAGGACCATACAGAGTGTGGGAA

CTGCTGGGGATCTAGGGAATTCAGTGGGACCAATGAAAGCATGGCTGAGAAATAGCAGGTAGTCCAGGAT

AGTCTAAGGGAGGTGTTCCCATCTGAGCCCAGAGATAAGGGTGTCTTCCTAGAACATTAGCCGTAGTGGA

ATTAACAGGAAATCATGAGGGTGACGTAGAATTGAGTCTTCCAGGGGACTCTATCAGAACTGGACCATCT

CCAAGTATATAACGATGAGTCCTCTTAATGCTAGGAGTAGAAAATGGTCCTAGGAAGGGGACTGAGGATT

GCGGTGGGGGGTGGGGTGGAAAAGAAAGTACAGAACAAACCCTGTGTCACTGTCCCAAGTTGCTAAGTGA

ACAGAACTATCTCAGCATCAGAATGAGAAAGCCTGAGAAGAAAGAACCAACCACAAGCACACAGGAAGGA

AAGCGCAGGAGGTGAAAATGCTTTCTTGGCCAGGGTAGTAAGAATTAGAGGTTAATGCAGGGACTGTAAA

ACCACCTTTTCTGCTTCAATATCTAATTCCTGTGTAGCTTTGTTCATTGCATTTATTAAACAAATGTTGT

ATAACCAATACTAAATGTACTACTGAGCTTCGCTGAGTTAAGTTATGAAACTTTCAAATCCTTCATCATG

TCAGTTCCAATGAGGTGGGGATGGAGAAGACAATTGTTGCTTATGAAAGAAAGCTTTAGCTGTCTCTGTT

TTGTAAGCTTTAAGCGCAACATTTCTTGGTTCCAATAAAGCATTTTACAAGATCTTGCATGCTACTCTTA

GATAGAAGATGGGAAAACCATGGTAATAAAATATGAATGATAAAA
```

Administration and Formulations

Active agents (e.g., IgG or other antibodies, Fc regions, small molecules) described herein can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) Advanced Organic Chemistry; Reactions, Mechanisms and Structure, 4$^{th}$ Ed. N.Y. Wiley-Interscience.

Methods of formulating such derivatives are known to those of skill in the art. For example, the disulfide salts of a number of delivery agents are described in PCT Publication WO 2000/059863, which is incorporated herein by reference. Similarly, acid salts of therapeutic antibodies, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain acid addition salts of the active agents herein include halide salts, such as may be prepared using hydrochloric or hydrobromic acids.

Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments, basic salts include alkali metal salts, e.g., the sodium salt, and copper salts.

For the preparation of salt forms of basic drugs, the $pK_a$ of the counterion is preferably at least about 2 pH lower than the $pK_a$ of the drug. Similarly, for the preparation of salt forms of acidic drugs, the $pK_a$ of the counterion is preferably at least about 2 pH higher than the $pK_a$ of the drug. This permits the counterion to bring the solution's pH to a level lower than the $pH_{max}$ to reach the salt plateau, at which the solubility of salt prevails over the solubility of free acid or base. The generalized rule of difference in $pK_a$ units of the ionizable group in the active pharmaceutical ingredient (API) and in the acid or base is meant to make the proton transfer energetically favorable. When the $pK_a$ of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments, preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants or prepared from an anhydride or an acid chloride by reaction with ammonia or a lower alkyl amine.

Active agents can be administered locally (e.g., topically) or systemically, depending on the indication. In various embodiments, administration is topical, transdermal, oral, buccal, sublingual, nasal (or otherwise inhaled), rectal, parenteral (e.g., intravenous), etc. The compositions can be administered in a variety of unit dosage forms depending upon the method of administration. Suitable unit dosage forms, include, but are not limited to powders, tablets, pills, capsules, lozenges, pulmonary dosage forms (e.g., pulmonary dosage forms such as solutions for nebulizers, micronized powders for metered-dose inhalers, and the like), suppositories, patches, nasal sprays, injectables, implantable sustained-release formulations, lipid complexes, etc.

The active agents described herein can also be combined with a pharmaceutically acceptable carrier (excipient) to form a pharmaceutical composition. In certain embodiments, pharmaceutically acceptable carriers include those approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent of the present invention is administered.

Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, BHT (butylated hydroxytoluene), chelating agents, low molecular weight proteins, protection and uptake enhancers such as lipids, compositions that reduce the clearance or hydrolysis of the active agents, or excipients or other stabilizers and/or buffers.

The active agent(s) can be formulated with other physiologically acceptable compounds, particularly for use in the preparation of tablets, capsules, gel caps, and the like can include, but are not limited to, binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active agent(s) and the resulting composition is compressed. If desired, the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, hydroxypropylmethylcellulose acetate succinate, and Eudragit (Evonik, Germany; methacrylic-acrylic copolymers).

Other physiologically acceptable compounds that can be included with the active agent(s) include wetting agents, emulsifying agents, dispersing agents or preservatives that are particularly useful for preventing the growth or action of microorganisms. Various preservatives are well known and include, for example, phenol and sorbic acid. One skilled in the art appreciates that the choice of pharmaceutically acceptable carrier(s), including a physiologically acceptable compound depends, for example, on the route of administration of the active agent(s) and on the particular physiochemical characteristics of the active agent(s).

In certain embodiments, the excipients are sterile and generally free of undesirable matter. These compositions can be sterilized by conventional, well-known sterilization techniques. For various oral dosage form excipients such as tablets and The dosage of active agent(s) can vary widely, and will be selected primarily based on activity of the active ingredient(s), body weight and the like in accordance with the particular mode of administration selected and the patient's needs. In various embodiments dosages can be provided ranging from about 0.1 or 1 mg/kg/day to about 50 mg/kg/day and sometimes higher. Typical dosages range from about 3 mg/kg/day to about 3.5 mg/kg/day, for example, from about 3.5 mg/kg/day to about 7.2 mg/kg/day, from about 7.2 mg/kg/day to about 11.0 mg/kg/day, or from about 11.0 mg/kg/day to about 15.0 mg/kg/day. In certain embodiments, dosages range from about 10 mg/kg/day to about 50 mg/kg/day. In certain embodiments, dosages range from about 20 mg to about 50 mg given orally twice daily. It will be appreciated that such dosages may be varied to optimize a therapeutic and/or prophylactic regimen in a particular subject or group of subjects.

In various embodiments, the active agent(s) is present in the formulation at a concentration ranging from about 1 nM, to about 1, 10, or 100 mM, more preferably from about 1 nM, about 10 nM, about 100 nM, about 1 or about 10 µM to about 50 about 100 about 200 about 300 about 400 or about 500 preferably from about 1 about 10 about 25 or about 50 µM to about 1 mM, about 10 mM, about 20 mM, or about 5 mM, most preferably from about 10 about 20 or about 50 µM to about 100 about 150 or about 200 µM.

In certain embodiments, the active agents of this invention are administered to the oral cavity. This is readily accomplished by the use of lozenges, aerosol sprays, mouthwash, coated swabs, and the like.

In certain embodiments the active agents of this invention are administered systemically (e.g., orally, or as an injectable) in accordance with standard methods well known to those of skill in the art. In other preferred embodiments, the agents, can also be delivered through the skin using conventional transdermal drug delivery systems, or transdermal drug delivery systems utilizing minimally invasive approaches (e.g., in combination with devices enabling microporation of upper layers of skin). Illustrative transdermal delivery systems include, but are not limited to transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active agent(s)" that is ultimately available for delivery to the surface of the skin. Thus, for example, the "reservoir" may include the active agent(s) in an adhesive on a backing layer of the patch, or in any of a variety of different matrix formulations known to those of skill in the art. The patch may contain a single reservoir, or it may contain multiple reservoirs.

In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the patch and provides the device with much of its flexibility. The material selected for the backing layer is preferably substantially impermeable to the active agent(s) and any other materials that are present.

Formulations for topical delivery include, but are not limited to, ointments, gels, sprays, fluids, creams, reconstituted extracellular matrix complexes, synthetic skin, and the like. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Active agents can also be delivered topically using reconstituted extracellular matrix complexes, such as Matrigel® (U.S. Pat. No. 4,829,000, which is incorporated by reference herein for its disclosure of these materials) or synthetic skin-type materials, such as those disclosed in International Pub. Nos. WO2015198002 and WO2013164635 and U.S. Pat. No. 9,514,658 (each of which is incorporated by reference herein for its disclosure of these materials).

In certain embodiments, one or more active agents of the present invention can be provided as a "concentrate", e.g., in a storage container (e.g., in a premeasured volume) ready for dilution, or in a soluble capsule ready for addition to a volume of water, alcohol, hydrogen peroxide, or other diluent.

While the invention is described with respect to use in humans, it is also suitable for animal, e.g., veterinary use. Thus certain preferred organisms include, but are not limited to humans, non-human primates, canines, equines, felines, porcines, ungulates, largomorphs, and the like.

Novel Cell Lines

Novel cell lines characterized by down-regulated expression of one or both of the FcγRIIA and/or FcγRIIIA receptors or in which the gene(s) for one or both receptors are knocked out have been produced, as described in Example 3. In various embodiments, such cell lines are FcγRIIA− and FcγRIIIA+, FcγRIIA+ and FcγRIIIA−, or FcγRIIA− and FcγRIIIA−. These cell lines are useful, for example, for elucidating the role of these two receptors in immune processes, such as flavivirus infection (as illustrated in Example 3).

In particular embodiments, any cells that naturally express these two receptors (i.e., that are FcγRIIA+ and FcγRIIIA+) can be used to produce one of more of these cells. Illustrative cell types include HEK 293T cells, A549 cells, K562 cells, THP-1 cells, U937 cells, MDCK cells Jurkat cells, Raji cells, BJAB cells, and monocytes/macrophages (such as the U937 cells described in Example 3). In various embodiments, the cells are mammalian, primate, or human cells.

EXAMPLE 1—Fc Glycan Analysis

Influenza hemagglutinin (HA)-specific IgGs were isolated from serum-purified IgG by HA affinity chromatography for mass spectrometric analysis of Fc glycoforms. Protein samples (10 µg) were denatured with 6M guanidine-HCl, reduced with 10 mM DTT at 56° C. for 45 min and alkylated with 60 mM iodoacetamide for 1 h followed by 30 min incubation with 20 mM DTT. The samples were trypsin digested (37° C. for 16 h) and desalted using solid phase extraction (SPE) on Sep-Pak Cartridges (Waters, Milford, MA). Tryptic peptides were eluted and evaporated to dryness in a Speedvac SC110 (Thermo Savant) before analysis. Fc glycoforms were specifically identified (Fab glycans excluded) based on tryptic peptide sequence identification. NanoLC-MS/MS analysis for characterization of glycosylation sites was performed on an UltiMate3000 nanoLC (Dionex) coupled with a hybrid triple quadrupole linear ion trap mass spectrometer, the 4000 Q Trap (AB SCIEX).

MS data acquisition was performed using Analyst 1.4.2 software (Applied Biosystems) for precursor ion scan triggered information dependent acquisition (IDA) analysis and enhanced MS-based IDA analysis (S. Zhang et al. (2012), Comparative characterization of the glycosylation profiles of an influenza hemagglutinin produced in plant and insect hosts, Proteomics, 12:1269-1288; S. Zhang, B. L. Williamson (2005), Characterization of protein glycosylation using chip-based nanoelectrospray with precursor ion scanning quadrupole linear ion trap mass spectrometry, Journal of biomolecular techniques: JBT, 16:209-219. The precursor ion scan of the oxonium ion (HexNAc+ at m/z 204.08) was monitored at a step size of 0.2 Da across a mass range of m/z 400 to 1600 for detecting glycopeptides containing N-acetylhexosamine unit. The nanospray voltage was 1.9 kV, and was used in positive ion mode for all experiments. The declustering potential was set at 50 eV and nitrogen as collision gas. In IDA analysis, after each precursor ion scan or EMS scan, and enhanced resolution scan, the two to three highest intensity ions with multiple charge states were selected for tandem MS (MS/MS) with rolling collision energy applied for detected ions based on different charge states and m/z values. All acquired MS/MS spectra from EMS-IDA were subjected to Mascot database search. All acquired MS/MS spectra for detected glycopeptides ions by precursor ion scanning were manually inspected and interpreted with Analyst 1.4.2 and BioAnalysis 1.4 software (Applied Biosystems). The peak areas of detected precursor ions were determined by extracted chromatogram (XIC) at each specific m/z representing glycopeptides isoforms. The relative quantitations of the sugar glycan isoforms of N-linked peptide ions were carried out based on precursor ion peak areas under assumption that all sugar glycan isoforms linked to the same core peptide have identical or a similar ionization efficiency. The eleven glycoforms analyzed were those present in greatest abundance within our sample set.

EXAMPLE 2—Abundance of Afucosylated Glycoforms on Anti-Dengue IgGs can be Used to Diagnose Susceptibility to Clinically Significant Dengue Disease New studies from our lab further support a role for elevated afucFc of anti-DENV IgGs in DENV disease. We studied anti-DENV IgGs from mothers of infants who had well-characterized DENV infections in the months following birth [8]. Because infants acquire maternal IgGs transplacentally during gestation, this study allowed us to address the question of how the pre-existing IgG repertoire (in infants) impacts susceptibility to DENV disease. We found that elevated maternal anti-DENV IgG (>10%) was a predictor of symptomatic infant DENV infection (FIG. 4) (PPV 88.8%). Together with our prior studies, this result supports a role for afucFc and FcγRIIIa in ADE of DENV disease and suggests that pre-existing anti-DENV IgGs can be used as a predictor of risk for clinically significant DENV disease. This finding indicates that the abundance of afucosylated glycoforms on anti-dengue IgGs can be used to diagnose susceptibility to clinically significant dengue disease.

EXAMPLE 3—Signaling Through FcγRIIIa Renders Cells More Susceptible to Infection Materials and Methods
Knock-out U937 cell lines where generated using the CRISPR-Cas9 system as follows: the gRNAs to target hCD32a and hCD32b were designed utilizing DESKGEN software, and inserted into sequence containing U6 promoter and gRNA scaffold (Yang, L., Yang, J. L., Byrne, S., Pan, J., & Church, G. M. (2014). CRISPR/Cas9-Directed Genome Editing of Cultured Cells. Current Protocols In Molecular Biology / Edited By Frederick M. Ausubel). The gRNA sequences to target hCD32a and hCD32b were 5'GATGTATGTCCCAGAAACCTG 3' (SEQ ID NO:1) and 5'GCATATGACCCCAAGGCTGGG3' (SEQ ID NO:2) respectively. The final fragments (Integrated DNA Technologies) were cloned into the pCR-BluntII-Topo vector. Human codon optimized cas9 DNA was obtained from Addgene (#41815). To generate the knockout cell lines, U937 cells were transfected with 1.5 μg hCas9 and 0.5 μg of gRNA via electroporation. The U937 cells were electroporated using Lonza 2b (program W-001) and the Nucleofector Kit C (VPA-1004, Lonza). After electroporation, U937 cells incubated at 37° C. for 48 hours. Following incubation, cells were synchronized at the early S phase using a double thymidine block. The cells were stained with IV.3-FITC (Stemcell), and CD32A negative cells were bulk sorted on SH800 sorter. After one bulk sort, the cells were single cell sorted based on negative CD32A expression. The single cell clones were confirmed using Sanger sequencing. Stable FcγRIIIa-expressing cell lines were produced by lentivirus transduction of the FcγRIIIa gene into wildtype or FcγRIIa-U937 cells (after CRISPR/Cas9 methods, as above).

Results and Discussion
Because afucosylated Fc glycans increase affinity of IgGs for one specific FcR, FcγRIIIa, our data point to FcγRIIIa in pathogenesis of DENV disease. To understand the role of this receptor in DENV infection, we generated cell lines that enabled us to isolate the role of FcγRIIIa during infection. Though major subsets of human monocytes (a primary host cell for DENV in vivo) express both activating FcγRs, FcγRIIa and FcγRIIIa, U937 cells and other cell lines that are commonly used to study ADE in vitro do not express FcγRIIIa [10, 11]. Thus, we generated a panel of human monocytic cell lines (U937) that express all combinations of the activating FcγRs, FcγRIIA and FcγRIIIA (FIG. 5).

Using these cell lines, we compared the outcome of infection mediated by FcγRIIa vs FcγRIIIa. Cells were infected with DENV2 virus in the presence of a normally fucosylated human IgG1 anti-DENV monoclonal antibody (DENV+wild type human IgG1 mAb 235). Cells that were negative for both FcγRIIa and FcγRIIIa (FcγRIIa-FcγRIIIa-) were infected at the same background level as cells that were FcγRIIa-FcγRIIIa+. This showed that FcγRIIIa (F158 allele) alone does not enhance infection with DENV+wild type human IgG1 mAb 235. Cells that were FcγRIIa+FcγRIIIa- were infected at a rate greater than twice background, showing enhanced infection in the presence of FcγRIIa alone. Cells that were double positive for FcγRIIa+FcγRIIIa+ were infected at a rate significantly higher than FcγRIIa+FcγRIIIa- cells, showing that the presence of FcγRIIIa enhances infection in FcγRIIa-expressing U937 cells (FIG. 6). The readout was conducted as follows: 24 hours after infection, cells were stained with live/dead fixable stain, fixed then stained for expression of dengue envelope protein. Cells were then analyzed by FACS for live, infected cells as a percent of total live cells.

Figure 7A:
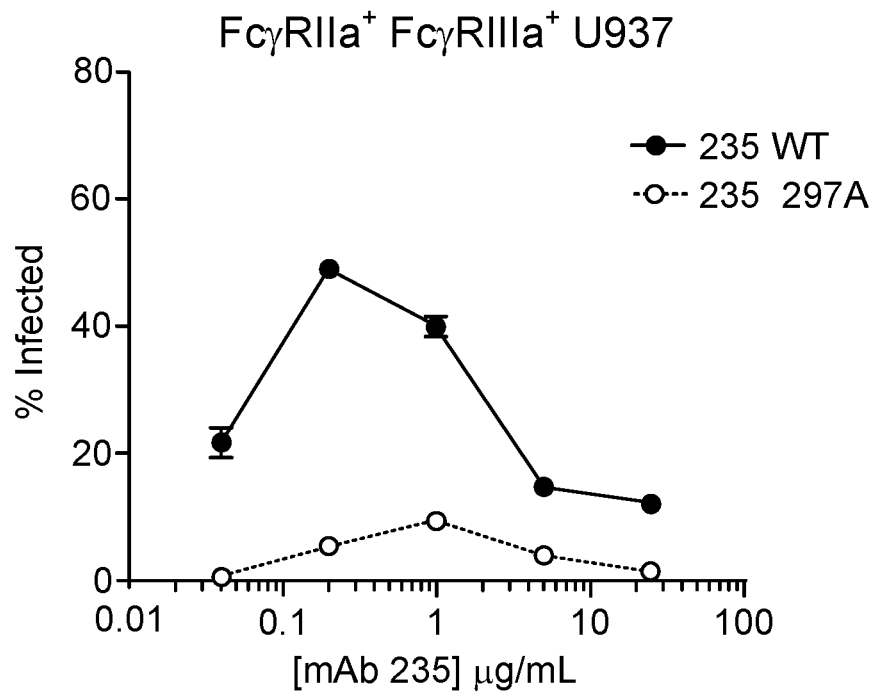
FIG. 7A-7B: (7A) DENV infection was enhanced in FcγRIIa+FcγRIIIa+ U937 cells when infection occurred in the presence of monoclonal antibody (mAb) 235 expressed as a human IgG1 (235 WT), but not in the presence of mAb 235 with non-binding Fc domain mutations N297A (235 297A). "mAb 235" is an alias for mAb D23-5G2D2 from Sasaki et al. Antiviral Res. 2013 June; 98(3):423-31. (7B) DENV+mAb 235 WT showed enhanced infection in FcγRIIa+FcγRIIIa− U937 cells; infection was further enhanced in cells that expressed FcγRIIa and FcγRIIIa (FcγRIIa+FcγRIIIa+)
Figure 7B:
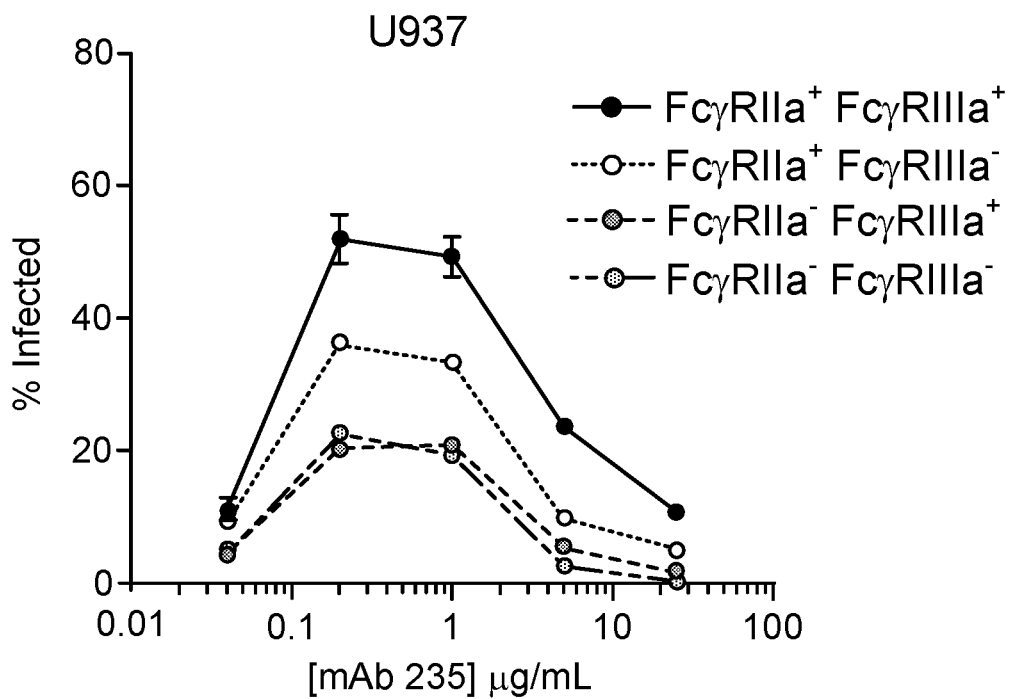
Figure 8A:
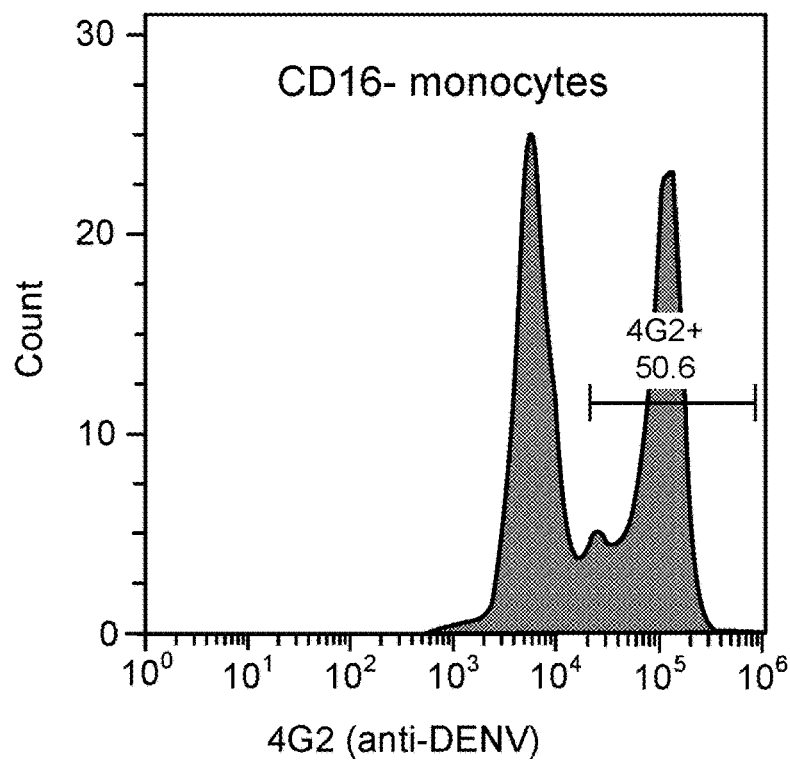
FIG. 8A-8B: Primary monocytes were sorted based on FcγRIIIa (CD16a) expression prior to infecting with DENV+mAb 235WT. As with U937 cells, FcγRIIIa+/CD16a+ primary monocytes (8B; which are also FcγRIIa+/CD32a+) showed increased infectability compared with FcγRIIIa−/CD16a− cells (8A).
Figure 8B:
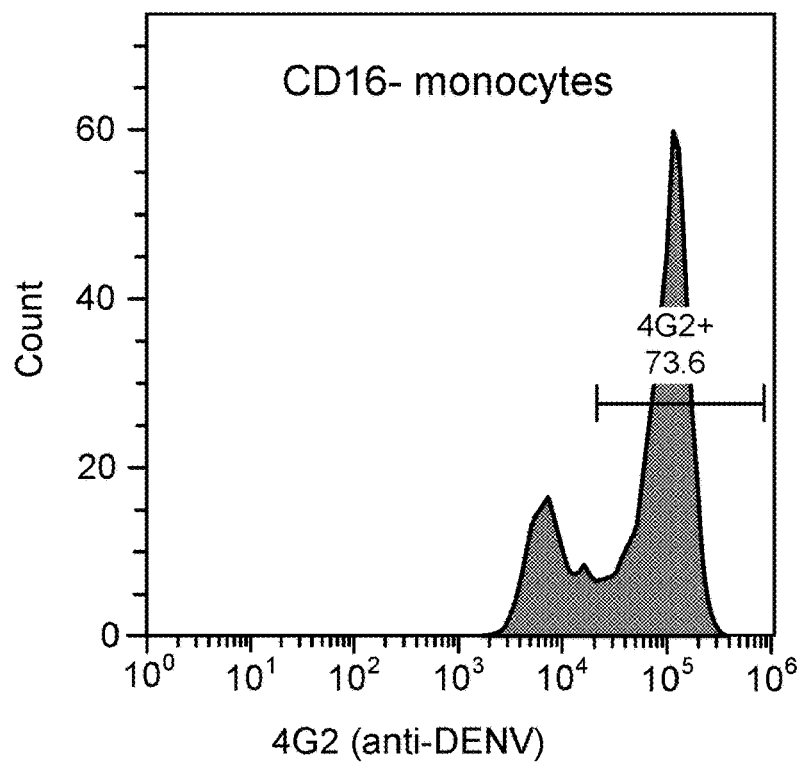
Figure 9A:
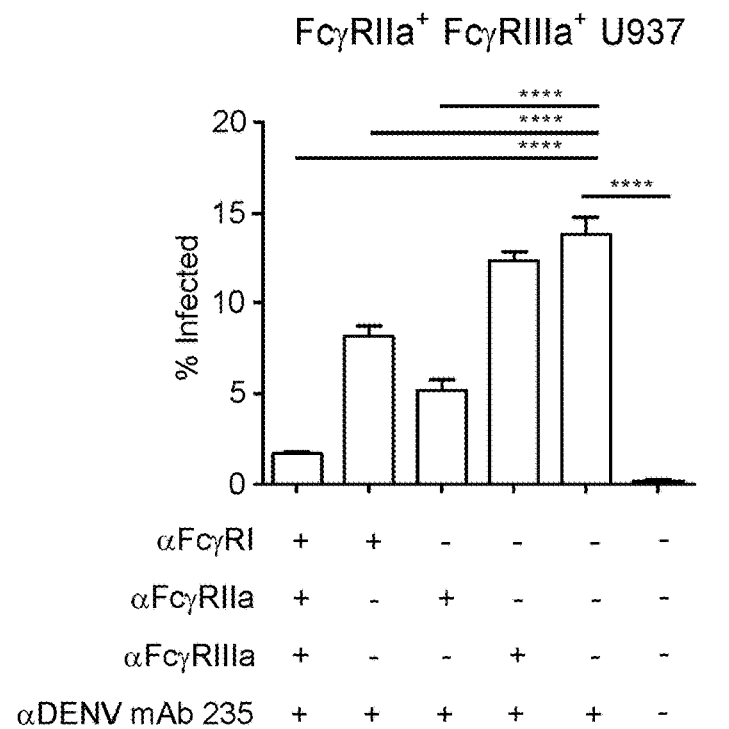
FIG. 9A-9B: Individual FcγRs were blocked using mAbs 10.1 (FcγRI), IV.3 (FcγRIIa), 2B6 (FcγRIIb) or 3G8 (FcγRIIIa) prior to infection of cells with DENV+mAb 235WT to determine which receptors' extracellular domains were required for ADE of DENV infection. (9A) Blocking FcγRIIa did reduce infection while blocking FcγRIIIa did not diminish infection in FcγRIIa+FcγRIIIa+ U937 cells. (9B) Blocking FcγRIIa reduced all infection in primary monocytes.'
Figure 9B:
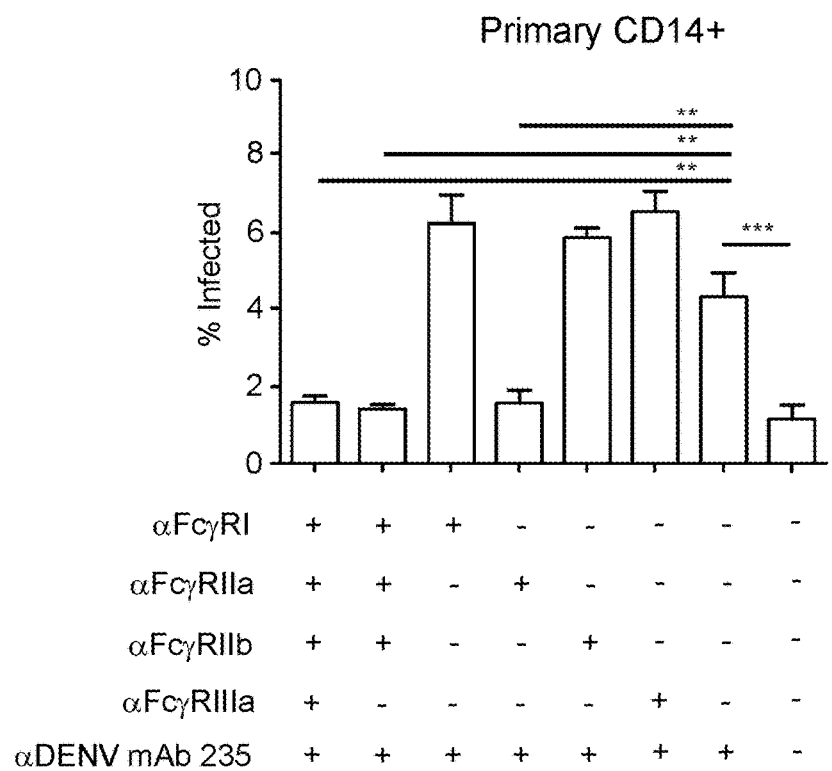
Figure 10:
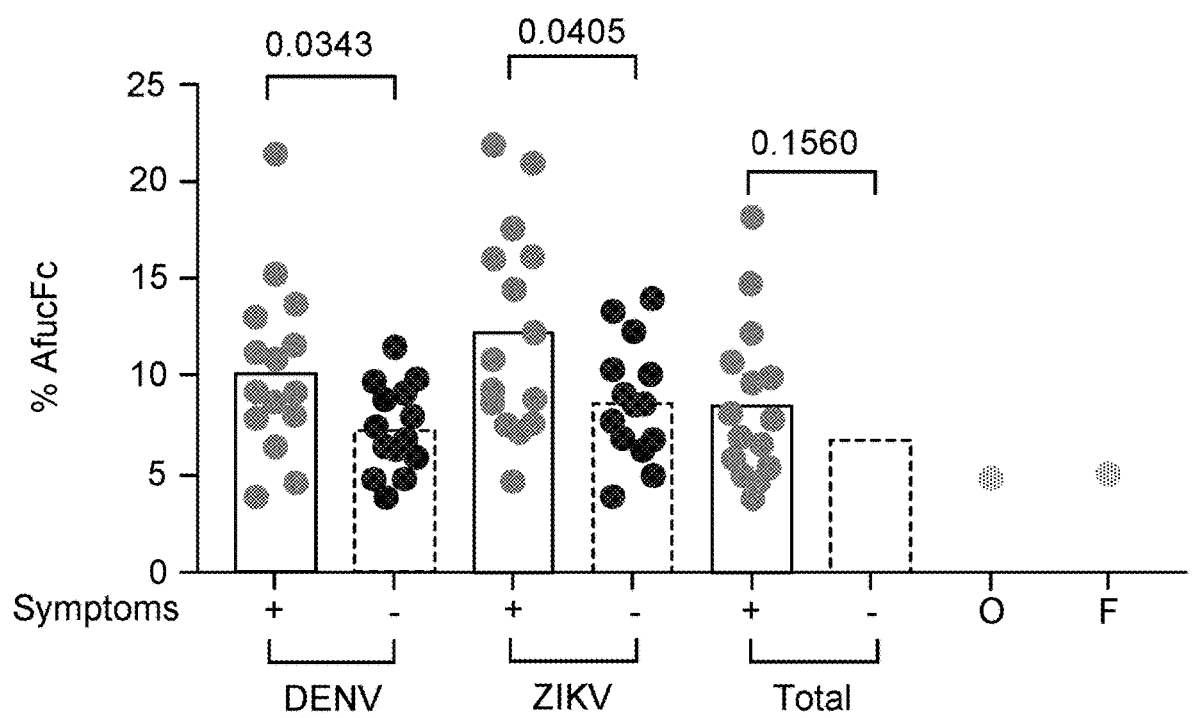
FIG. 10: Maternal anti-DENV IgG, % afucosylation (afucFc). Maternal afucFc anti-dengue IgG1≥10% is a risk factor for symptomatic dengue infection in infant (p=0.0352). Positive predictive value: 87.5% (95% CI 52.9%-99.3%). The abundance of afucFc on Zika-reactive maternal IgGs also correlated with risk (Zika and dengue are antigenically cross-reactive).

We next performed the infections in CD16+ and CD16- primary human monocytes. To do this, monocytes were sorted into CD16+ and CD16- populations and infected with DENV+mAb235 for 24 hours. Consistent with the experiments in the U937 cell lines, CD16+ monocytes were more susceptible to infection (FIG. 7). This data shows that the presence of CD16 on a monocyte cell line or on primary human monocytes mediates enhanced DENV infection. There are two main mechanisms by which this might occur. First, DENV-IgG complexes could bind to FcγRIIIa and mediate enhanced uptake. Or, FcγRIIIa signaling (basal signaling) could increase the potential for infection of cells.

To determine whether binding of DENV-IgG was required, we used blocking antibodies against FcRs on U937 prior to infection with DENV+DENV+wild type human IgG1 mAb 235. While blocking binding to FcγRIIa (CD32a) reduced infection significantly, blocking FcγRIIIa (CD16a) did not. This indicates that basal signaling through FcγRIIIa renders cells more susceptible to infection. This finding indicates that inhibitors of FcγRIIIa signaling could be used to prevent enhancement of DENV infection.

Finally, referring to FIG. 11, we infected the cell lines with DENV+wild type human IgG1 mAb 235 (235 WT) or a partially afucosylated Fc 235 mAb (235 afuc). Afucosylation did not enhance infectability of FcγRIIa+FcγRIIIa+ cells (FIG. 11A), but did enhance virus replication as measured by infectious virus (pfu/mL) in the supernatant after 24 hrs in those cells (FIG. 11B). In cells that were FcγRIIa-FcγRIIIa+, DENV+235 afuc did show enhanced infectability (FIG. 11C) as well as increased virus replication (FIG. 11D), measured by infectious virus in supernatant at 24 hours post infection. These data show that the enhanced affinity of afucosylated Fc for FcγRIIIa in the context of infection by DENV-IgG immune complexes enhances virus replication in CD16+ cells. One possible mechanisms that could increase virus replication is antagonism of an interferon signaling pathway in the presence of basal FcγRIIIa signaling that is enhanced by interactions with afucosylated Fc domains.

EXAMPLE 4—Selective Requirement by Dengue Viruses for ITAM/NFAT Signaling Pathway We next designed studies to investigate how signaling through ITAM domains by activating FcγRs impacts dengue infections. Crosslinking of activating FcγRs by immune complexes triggers a signaling cascade including tyrosine phosphorylation of ITAMs by Src kinases followed by recruitment and activation of spleen tyrosine kinase (Syk). (See FIG. 11.) Downstream activation of NFκB and MAPKs follows, along with calcium signaling that activates the phosphatase calcineurin, in turn activating nuclear factor of activated T cells (NFAT) transcription factors that control a host of immune-regulatory genes (references 10, 11, below). Activation of NFAT transcription factors has specifically been observed after ligation of FcγRIIIa on NK cells (reference 12).

Figure 12A:
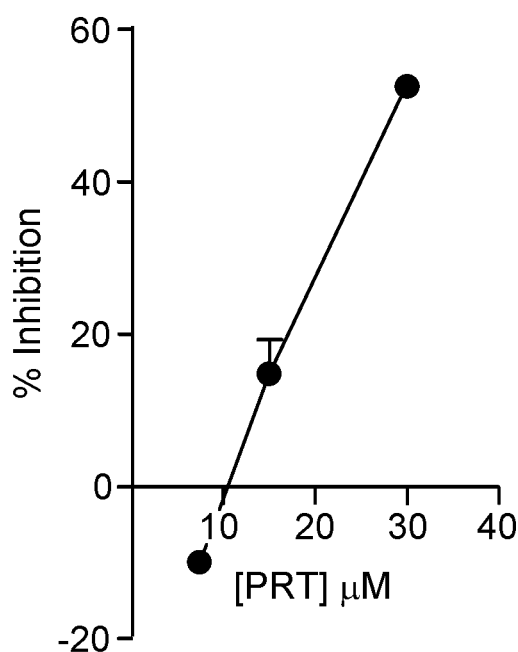
FIG. 12A-12G: Inhibition of dengue infection through targeted inhibition of ITAM signaling pathway elements. To study how signaling by activating FcγRs might enhance dengue infection, we asked whether dengue could be inhibited using inhibitors of the ITAM signaling pathway. (A) A small-molecule inhibitor that targets SYK (PRT) inhibited dengue 2 infection in FcγRIIa+FcγRIIIa+ monocytes in a concentration-dependent manner. (B) A peptide inhibitor, 11R-VIVIT (VIVIT), that specifically inhibits activation of NFAT transcription factors by calcineurin, but not a control peptide containing the amino acids found in VIVIT but in a scrambled sequence (VEET), inhibited dengue 2 infection in a concentration-dependent manner. VIVIT in solid lines, VEET in dotted lines. (C) Inhibition with 5 μM NFAT peptide was sufficient to inhibit dengue 2 infection at all MOIs tested by >70%. (D) Activation of the NFAT-regulated genes can be studied by treatment of cells with phorbol ester (PMA) plus ionomycin. PMA and ionomycin treatment of FcγRIIa+FcγRIIIa– U937 cells enhanced dengue 2 infection in a concentration dependent manner. (E) Enhanced infection after PMA/ionomycin treatment could be inhibited by the NFAT inhibitor, VIVIT. (F) Treatment of cells up to 2 hours following infection inhibited dengue 2 replication implicating NFAT-regulated gene(s) in enhancement of a post-binding and entry step of viral replication. (G) Next we determined whether basal NFAT signaling in cells permissible to dengue infection in the absence of antibodies was required for replication. DC-SIGN U937 cells are human monocytes that are infectible by dengue viruses without antibodies present. NFAT inhibition by VIVIT (solid lines) but not the scrambled peptide, VEET (dotted lines) was observed against dengue 3 (DENV3), but VIVIT did not inhibit Zika virus infection (ZIKV), or H1N1 or H3N2 influenza virus infection (IAV).
Figure 12B:
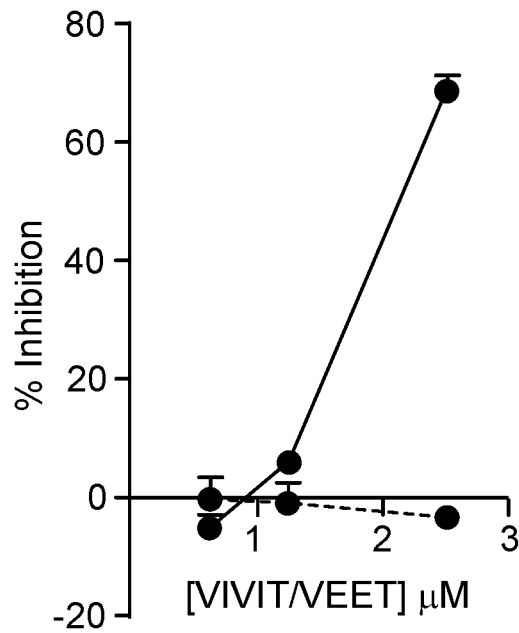
Figure 12C:
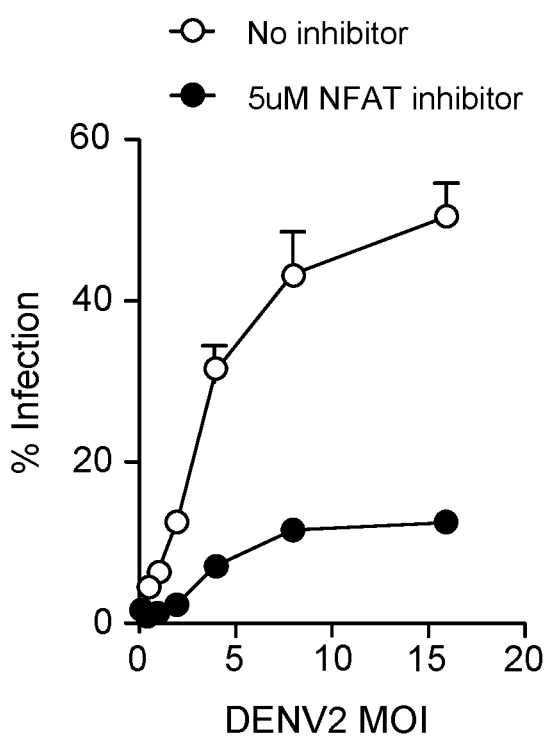
Figure 12D:
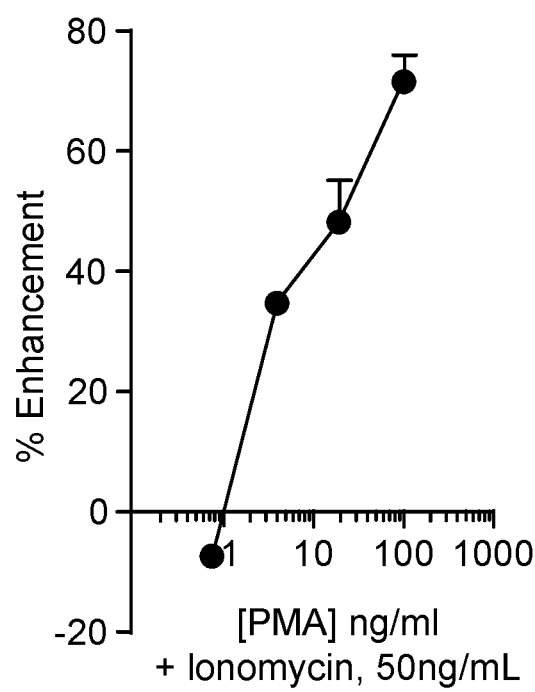
Figure 12E:
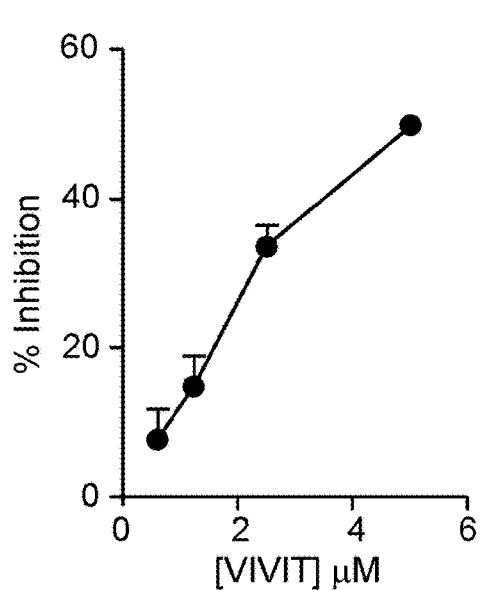
Figure 12F:
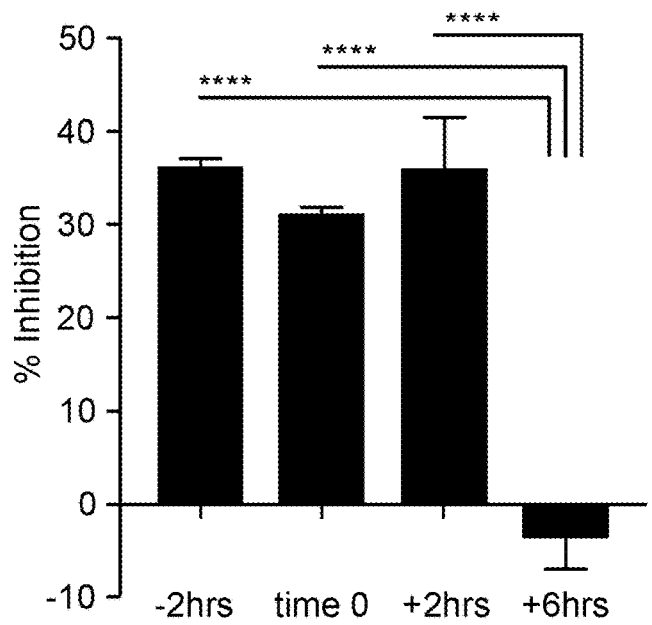
Figure 12G:
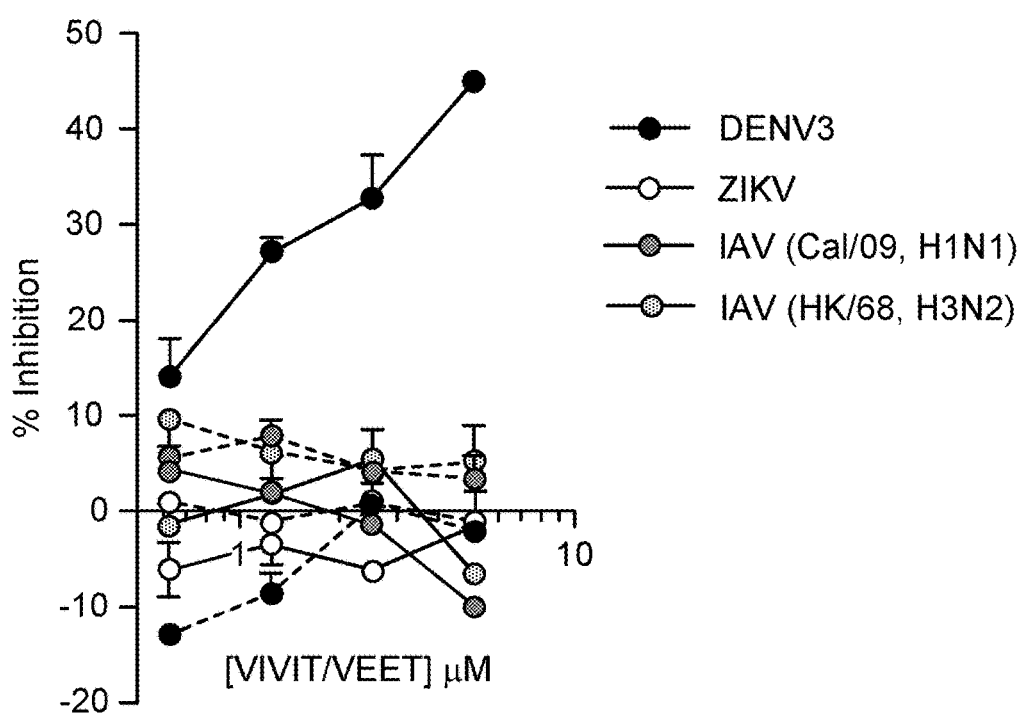

We first asked whether dengue infection could be inhibited using the small-molecule Syk inhibitor, PRT318 (PRT) (M. P. Reilly et al., PRT-060318, a novel Syk inhibitor, prevents heparin-induced thrombocytopenia and thrombosis in a transgenic mouse model. Blood 117, 2241-2246 (2011), which is hereby incorporated by reference herein for this description). Indeed, ADE of dengue infection was inhibited in FcγRIIa+FcγRIIIa+ monocytes in a concentration-dependent manner by PRT (FIG. 12A). Next, we evaluated the role of downstream activation of the NFAT transcription factors by calcineurin in dengue infection. To study this, we selected a peptide inhibitor, 11R-VIVIT (VIVIT), which specifically inhibits activation of NFAT transcription factors by calcineurin without impacting NFκB signaling as other NFAT inhibitors do (J. Aramburu et al., Affinity-driven peptide selection of an NFAT inhibitor more selective than cyclosporin A. Science 285, 2129-2133 (1999), which is hereby incorporated by reference herein for this description). Pre-incubation of FcγRIIa+FcγRIIIa+ monocytes with VIVIT but not with a control peptide containing the amino acids found in VIVIT but in a scrambled sequence (VEET), inhibited dengue infection in a concentration-dependent manner (FIG. 12B). Cell viability was unaffected at concentrations tested. Inhibition with 5 µM NFAT peptide (VIVIT) was sufficient to inhibit dengue infection at all MOIs tested by >70% (FIG. 12C). Activation of the NFAT-regulated genes can be studied by treatment of cells with phorbol ester (PMA) plus ionomycin (reference 15). Inhibition of ADE in FcγRIIa+FcγRIIIa+, downstream of Syk activation, was required for modulates dengue infection. PMA and ionomycin treatment of FcγRIIa+FcγRIIIa− U937 cells enhanced dengue 2 infection in a concentration dependent manner (FIG. 12D). Enhanced infection after PMA/ionomycin treatment could be inhibited by the NFAT inhibitor, VIVIT (FIG. 12E). Treatment of cells up to 2 hours following infection inhibited dengue 2 replication implicating NFAT-regulated gene(s) in enhancement of a post-binding and entry step of viral replication. (FIG. 12F.) Next, we determined whether basal NFAT signaling in cells permissible to dengue infection in the absence of antibodies was required for replication. DC-SIGN U937 cells are human monocytes that are infectible by dengue viruses without antibodies present. NFAT inhibition by VIVIT (solid lines) but not the scrambled peptide, VEET (dotted lines) was observed against dengue 3 (DENV3), but VIVIT did not inhibit Zika virus infection (ZIKV), or H1N1 or H3N2 influenza virus infection (IAV) (FIG. 12G).

EXAMPLE 5—Mechanism of Enhancement of Infectability by FcγRIIIa

Figure 13:
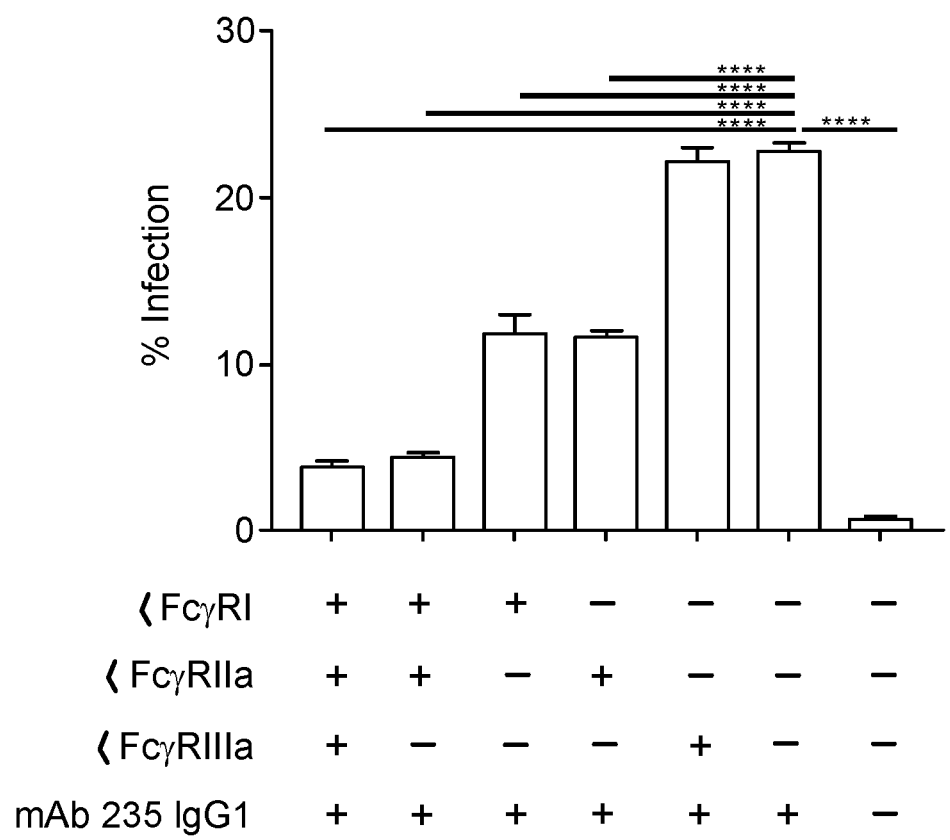
FIG. 13: Mechanism of enhancement of infectability by FcγRIIIa. To determine whether the presence of FcγRIIIa enhances infectability of FcγRIIa$^+$ FcγRIIIa$^+$ cells by increasing virus binding to host cells or virus entry, FcγRs were individually blocked during infection. Blocking all activating FcγRs during infection reduced infection by >85%. Blocking FcγRIIa alone decreased infection by >60%, while blocking FcγRIIIa alone or in combination with blocking antibodies against FcγRI and FcγRIIa did not significantly impact infection demonstrating that enhancement by FcγRIIIa is likely achieved through entry-independent mechanism(s).

To determine whether the presence of FcγRIIIa enhances infectability of FcγRIIa+ FcγRIIIa+ cells by increasing virus binding to host cells or virus entry, FcγRs were individually blocked during infection (FIG. 13). Blocking all activating FcγRs during infection reduced infection by >85%. Blocking FcγRIIa alone decreased infection by >60%, while blocking FcγRIIIa alone or in combination with blocking antibodies against FcγRI and FcγRIIa did not significantly impact infection demonstrating that enhancement by FcγRIIIa is likely achieved through entry-independent mechanism(s).

REFERENCES

1. Rodrigo, W. W., et al., Differential enhancement of dengue virus immune complex infectivity mediated by signaling-competent and signaling-incompetent human Fcgamma RIA (CD64) or FcgammaRIIA (CD32). J Virol, 2006. 80(20): p. 10128-38.
2. Wang, T. T., et al., IgG antibodies to dengue enhanced for FcgammaRIIIA binding determine disease severity. Science, 2017. 355(6323): p. 395-398.
3. Wang, T. T., et al., Anti-HA Glycoforms Drive B Cell Affinity Selection and Determine Influenza Vaccine Efficacy. Cell, 2015. 162(1): p. 160-9.
4. Maamary, J., et al., Increasing the breadth and potency of response to the seasonal influenza virus vaccine by immune complex immunization. Proc Natl Acad Sci USA, 2017.
5. Pfeifle, R., et al., Regulation of autoantibody activity by the IL-23-TH17 axis determines the onset of autoimmune disorder. Nat Immunol, 2016.
6. Brodin, P., et al., Variation in the human immune system is largely driven by non-heritable influences. Cell, 2015. 160(1-2): p. 37-47.
7. Fleit, H. B., S. D. Wright, and J. C. Unkeless, Human neutrophil Fc gamma receptor distribution and structure. Proc Natl Acad Sci USA, 1982. 79(10): p. 3275-9.

8. Jones, D. H., R. J. Looney, and C. L. Anderson, Two distinct classes of IgG Fc receptors on a human monocyte line (U937) defined by differences in binding of murine IgG subclasses at low ionic strength. J Immunol, 1985. 135(5): p. 3348-53.
9. Seeling, et. Al. (2017), Differential antibody glycosylation in autoimmunity: sweet biomarker or modulator of disease activity, Nature Reviews/Rheumatology, 13:621-630.
10. P. G. Hogan, L. Chen, J. Nardone, A. Rao, Transcriptional regulation by calcium, calcineurin, and NFAT. Genes Dev 17, 2205-2232 (2003).
11. L. B. Ivashkiv, Cross-regulation of signaling by ITAM-associated receptors. Nature immunology 10, 340-347 (2009).
12. J. Aramburu, L. Azzoni, A. Rao, B. Perussia, Activation and expression of the nuclear factors of activated T cells, NFATp and NFATc, in human natural killer cells: regulation upon CD16 ligand binding. The Journal of experimental medicine 182, 801-810 (1995).
13. M. P. Reilly et al., PRT-060318, a novel Syk inhibitor, prevents heparin-induced thrombocytopenia and thrombosis in a transgenic mouse model. Blood 117, 2241-2246 (2011).
14. J. Aramburu et al., Affinity-driven peptide selection of an NFAT inhibitor more selective than cyclosporin A. Science 285, 2129-2133 (1999).
15. E. Hooijberg, A. Q. Bakker, J. J. Ruizendaal, H. Spits, NFAT-controlled expression of GFP permits visualization and isolation of antigen-stimulated primary human T cells. Blood 96, 459-466 (2000).

What is claimed is:

1. A vaccination method, the method comprising:
   (a) performing an assay to determine a level of afucosylated Fc glycans in IgG antibodies in a biological sample from a subject or in a biological sample from mother of an infant subject, thereby identifying the subject not having 5 percent or greater of the IgG antibodies having the afucosylated Fc glycans in the biological sample from the subject, or identifying the infant subject with the mother not having 5 percent or greater of the IgG antibodies of the IgG antibodies having the afucosylated Fc glycans in the biological sample from the mother of the infant subject; and
   vaccinating against a Dengue virus the subject or the infant subject identified in step (a).

2. The vaccination method of claim 1, wherein the IgG antibodies are IgG1 antibodies.

3. The vaccination method of claim 1, wherein the IgG antibodies are IgG antibodies specific for a Dengue virus antigen.

4. The vaccination method of claim 1, wherein the 5 percent or greater is as 10 percent or greater.

5. The vaccination method of claim 1, wherein the vaccinating is vaccinating the infant subject.

6. The method of claim 1, wherein the IgG antibodies are IgG antibodies of all specificities.

7. The vaccination method of claim 1, wherein the subject is a human.

8. The method of claim 5, wherein the mother of the infant subject has IgG antibodies that are reactive with the Dengue virus.

9. The vaccination method of claim 1, wherein the biological sample is blood or a blood fraction.

* * * * *

UNITED STATES PATENT AND TRADEMARK OFFICE
CERTIFICATE OF CORRECTION

PATENT NO. : 11,826,414 B2
APPLICATION NO. : 16/758364
DATED : November 28, 2023
INVENTOR(S) : Taia T. Wang It is certified that error appears in the above-identified patent and that said Letters Patent is hereby corrected as shown below:

In the Claims

In Claim 1, In Column 57, Line 19:
Delete "of the IgG antibodies of the IgG antibodies" and
Insert -- of the IgG antibodies --.

In Claim 1, In Column 57, Line 22:
Delete "vaccinating" and
Insert -- (b) vaccinating --.

In Claim 4, In Column 58, Line 13:
Delete "is as" and
Insert -- is --.

Signed and Sealed this
Ninth Day of January, 2024

Katherine Kelly Vidal
*Director of the United States Patent and Trademark Office*